US009333037B2

(12) United States Patent
Loeb

(10) Patent No.: US 9,333,037 B2
(45) Date of Patent: May 10, 2016

(54) METHOD FOR EFFECTIVE AND UNIFORM FAT CELL LYSING AND MELTING OF THE RELEASED FAT

(71) Applicant: Trimedyne, Inc., Irvine, CA (US)

(72) Inventor: Marvin P. Loeb, Laguna Woods, CA (US)

(73) Assignee: Trimedyne, Inc., Irvine, CA (US)

( * ) Notice: Subject to any disclaimer, the term of this patent is extended or adjusted under 35 U.S.C. 154(b) by 221 days.

(21) Appl. No.: 14/039,914

(22) Filed: Sep. 27, 2013

(65) Prior Publication Data

US 2014/0088488 A1 Mar. 27, 2014

Related U.S. Application Data

(60) Provisional application No. 61/706,524, filed on Sep. 27, 2012.

(51) Int. Cl.
*A61B 19/00* (2006.01)
*A61B 18/20* (2006.01)
*A61N 5/067* (2006.01)

(52) U.S. Cl.
CPC ......... *A61B 18/20* (2013.01); *A61B 2018/2005* (2013.01); *A61N 2005/067* (2013.01)

(58) Field of Classification Search
CPC ........ A61B 18/20; A61B 18/22; A61B 18/24; A61B 18/201; A61B 18/203; A61B 2018/22272; A61B 2018/2288; A61B 2018/00315; A61B 2018/00009; A61B 2018/00625

USPC ............... 606/3, 13–17; 604/20, 21, 27, 28; 128/898

See application file for complete search history.

(56) References Cited

U.S. PATENT DOCUMENTS

| 5,437,660 | A  | * | 8/1995 | Johnson et al. | 606/15 |
| 5,649,924 | A  | * | 7/1997 | Everett et al. | 606/15 |
| 2005/0222681 | A1 | * | 10/2005 | Richley et al. | 623/17.11 |
| 2007/0179485 | A1 | * | 8/2007 | Yeik et al. | 606/15 |

* cited by examiner

*Primary Examiner* — Ahmed Farah
(74) *Attorney, Agent, or Firm* — Olson & Cepuritis, Ltd.

(57) ABSTRACT

Lysing of fat cells in adipose tissue beneath the skin and liquefying the released fat is achieved by introducing a side-firing thermal energy device into the tissue to be irradiated, while thermal energy, such as laser energy, is emitted at a selected level for a selected period of time, depending on the volume to tissue to be irradiated. The side firing device is advanced into tissue and withdrawn and, while energy is emitted, is aimed separately at 3 o'clock and 9 o'clock and, is repetitively rotated through an arc of about 120°, producing a bowtie-shaped irradiation pattern. The side firing device may be centered and sealingly held in position in a liposuction cannula by ribs extending inwardly from the interior of the liposuction cannula. At least one of the ribs has a channel for infusion of an irrigating liquid. The use of laser energy during lysis of fat cell membranes and the liquefaction of the released fat also produces photomechanical cross-linking of collagen, which shrinks and tightens the skin, reducing sagging of the skin after removal or absorption of the liquefied fat. Nucleus pulposus tissue can be vaporized in a similar manner.

8 Claims, 8 Drawing Sheets

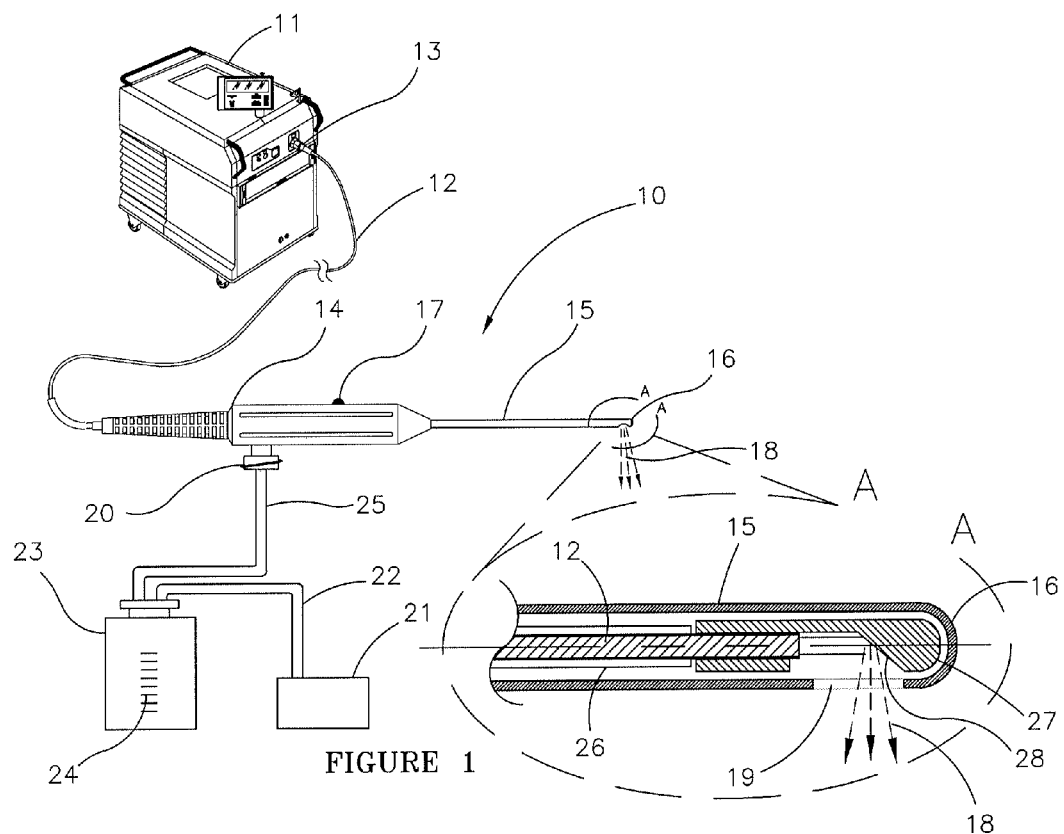
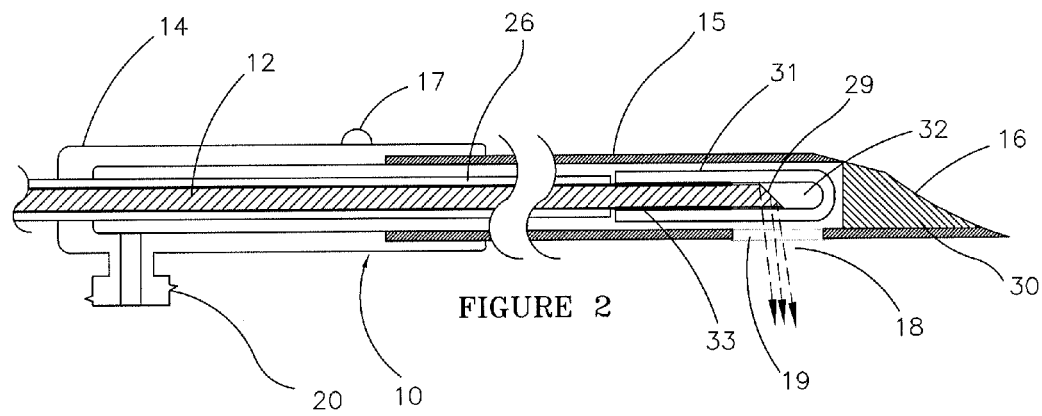
FIGURE 1
FIGURE 2

METHOD FOR EFFECTIVE AND UNIFORM FAT CELL LYSING AND MELTING OF THE RELEASED FAT

CROSS-REFERENCE TO RELATED APPLICATION

This application claims the benefit of U.S. Provisional Application No. 61/706,524, filed on Sep. 27, 2012, which is incorporated herein by reference in its entirety.

FIELD OF THE INVENTION

This invention relates to lysing of fat cells and melting the released fat, utilizing specially constructed side-firing laser devices and novel methods of use to produce safe, effective and uniform fat removal for an appealing cosmetic effect.

BACKGROUND OF THE INVENTION

Liposuction, also known as lipoplasty, involves the insertion of a hollow cannula into adipose or fatty tissue beneath the skin, usually accompanied by the injection of a fluid typically containing a local anesthetic and a vasoconstrictor and, optionally, an antibiotic, known as tumescent liposuction, to mechanically extract globules of fat by applying a vacuum to the cannula and sucking the fatty tissue into the cannula through a side vacuum port near the cannula's distal end.

The distal edge of the side vacuum port is sharp and, when globules of fat are drawn by suction into the vacuum port and the cannula is rapidly pulled backward, the sharp edge cuts off the globules of fat, which are evacuated by suction through the cannula into a collection bottle. However, when the cannula is rapidly pulled back, the sharp distal edge of the port also cuts blood vessels running through the fatty tissue, which can cause significant bleeding and increase the risk of an infection.

For example, an anesthetic such as lidocaine at a dosage of about 35 mg per kilogram of body weight, or a vasoconstrictor, such as epinephrine at a dosage of about 0.7 mg per kilogram of body weight, are commonly used in tumescent liposuction procedures to anesthetize and help separate tissues by constriction during the liposuction procedure. An antibiotic may be added to reduce the risk of an infection.

In the late 1990s, ultrasound energy was introduced to facilitate the fat removal process by liquefying globules of fat, but complications tempered the initial enthusiasm of many practitioners. Recently, laser energy to melt and liquefy fat has been introduced, which also has the benefit of less bleeding, as the laser energy can coagulate blood vessels in the fatty tissue, which are broken or cut during the liposuction process.

The use of laser energy to lyse (disrupt) the membranes of adipocytes (fat cells), soften and liquefy the released fat, called laser lipolysis, is presently performed in three different laser fat removal procedures. In the most preferred laser fat removal procedure, laser energy is transmitted from a laser through an optical fiber disposed within a hollow liposuction cannula. The optical fiber extends up to a side port in the wall of the liposuction cannula near its distal end. The port may or may not have a sharp proximal edge.

As adipose (fatty) tissue is drawn by suction into the side port in the liposuction cannula, laser energy is emitted straight ahead, lyses the membranes of the fat cells and softens or liquefies the released fat, which is drawn through the liposuction cannula into a collection bottle by vacuum. Most of the blood vessels in the fatty tissue which are broken or cut are coagulated (cauterized) by the laser energy. The released fat is evacuated into a collection bottle by vacuum. If the side port in the liposuction cannula does not have a sharp distal edge, this fat removal process is less traumatic than a conventional liposuction procedure.

In some laser liposuction procedures the distal end of the liposuction cannula is open or partially open, and the optical fiber extends up to open or partially open distal end of the liposuction cannula. As the cannula is advances and/or withdrawn, laser energy lyses fat cells opposite the distal end of the cannula and the released fat is drawn into the cannula and evacuated by suction. Again, blood vessels broken or cut during the procedure are coagulated (cauterized) by the laser energy.

Another benefit of the use of laser energy in a liposuction procedure is the fat is quickly removed and little is able to be absorbed into the bloodstream, avoiding an increase in the cholesterol and triglyceride levels in the patient's bloodstream.

In the second laser fat removal procedure, the optical fiber, optionally contained in a metal or rigid plastic cannula with an open distal end for better handling, without suction, is used to transmit laser energy straight ahead from the distal end face of the optical fiber to lyse the membranes of fat cells, soften and liquefy the fat. The optical fiber is inserted through a trocar puncture or surgically created opening and is advanced and withdrawn one or more times, and is withdrawn almost to the insertion point, and is then advanced and withdrawn at a series of different angles, like the ribs of a fan.

At the end of the laser procedure, the optical fiber is removed from the body, and a conventional liposuction cannula is introduced to evacuate the softened or melted fat. However, performing these procedures separately takes longer than the preferred procedure described above, and some of the softened or liquefied fat may be missed by the liposuction cannula and left in place, some of which may be absorbed into the bloodstream, which may raise the level of cholesterol and triglycerides in the bloodstream.

In the third laser fat removal procedure, the optical fiber again may be contained in an outer metal or rigid plastic cannula for ease of handling. The optical fiber is introduced and laser energy is emitted straight ahead from the distal end face of the optical fiber to lyse the membranes of the fat cells and soften or liquefy the fat, as described above. No suction or vacuum is used in this procedure. After removal of the optical fiber is removed from the body, some or most of the fat may be absorbed in the bloodstream and delivered to the liver, where it is said to be metabolized in the same manner as fat from the diet. It is not known if the larger volume of cholesterol and triglycerides in the bloodstream arising from this procedure is deleterious or not.

Laser energy emitted directly ahead from the flat distal end of a conventional optical fiber does not greatly diverge, so many insertions of the optical fiber at various angles are required. Also the same pattern of insertions is required, if a liposuction cannula is introduced to remove the melted fat, during or following the fat cell lysing procedure.

While the relative safety and efficacy of these three procedures, to our knowledge, has not been published, cosmetic surgeons and dermatologists experienced in using one or more of these procedures must evaluate which of them will best serve the needs of each individual patient. If the amount of laser energy is properly controlled, most blood vessels in the fatty tissue, which are cut or broken during the procedure, are coagulated by the laser energy, and little bleeding beneath the skin occurs.

At wavelengths of 300 to 400 nanometers ("nm"), for example, from an excited dimer or "excimer" laser at 308 or 351 nm, the laser energy is highly absorbed by molecular bonds, causing fat cell membranes to be disrupted and the released fat to be melted. At wavelengths of 1400 to 1500 nm and 1800 to 2300 mu, for example, from a diode laser at 1470 nm, a Thulium:YAG laser at 2000 nm or a CTH:YAG laser at 2100 nm, the laser energy is highly absorbed by water, which is almost instantly heated, disrupting the membranes of the fat cells and melting the released fat.

At wavelengths of 400 to 1400 and 1500 to 1800, the laser energy is minimally absorbed by pigments, for example hemoglobin in blood or melanin, until a temperature sufficient to disrupt the membranes of fat cells and melt the released fat.

In this patent application, our objective is to maximize the ability to lyse fat cells and vaporize tissue by combining improved devices for delivering laser energy with an optimal method of use of such devices to accomplish the desired purpose: safe, uniform and effective lysing of fat cells and melting of the released fat.

It is a further objective of this invention to provide a laser energy delivery device and a method of its use to more safely and effectively lyse the membranes of a greater number of fat cells beneath the dermis and soften or liquefy a greater volume of the released fat over a wider area in a more uniform manner than is possible with a straight-ahead firing optical fiber. It is another objective of this invention to do so without endangering the dermis at 12 o'clock and blood vessels, nerves and other delicate structures at 6'o clock.

The present invention attains these objectives in a safe and effective manner.

SUMMARY OF THE INVENTION

Membranes of fat cells that constitute adipose tissue are lysed by the laser energy with concurrent infusion of an irrigating liquid. The released fat is softened or melted (liquefied) by the laser energy. The liquefied fat is simultaneously withdrawn through the side port in the liposuction cannula and evacuated by vacuum or suction.

A conventional optical fiber, whose distal end portion has been uniquely constructed to emit laser energy of desired wavelengths at an angle of about 70° to 90° from the axis of the optical fiber, generally referred to as a "side firing device", can be used to lyse or vaporize adipose tissue. The side firing device also enables laser energy to be emitted with a greater divergence angle than from a conventional, straight-ahead firing optical fiber.

In a preferred embodiment for lysing of fat cells and melting or liquefying the released fat in a liposuction procedure, a side firing device is disposed within the central channel of a hollow, liposuction cannula, with a side port that enables the laser energy to be emitted laterally from the axis of the optical fiber and the liposuction cannula.

The liposuction cannula can be made of a rigid plastic or a metal, preferably medical grade stainless steel.

The present invention enables fat to be removed in a more safe and effective manner than prior art laser liposuction procedures, as described above. Furthermore the present invention provides a means for uniformly removing a larger volume of fat, for a more cosmetically appealing effect.

The present invention also enables the side firing device to be used by itself in the manner described above, being immediately followed by a separate liposuction procedure to remove the softened or liquefied fat, or used by itself in the manner described above, without being followed by a liposuction procedure, allowing the liquefied fat to possibly enter the bloodstream and be carried to the liver and/or intestines, where it may be metabolized.

In one embodiment of the present invention, the proximal end of a conventional, end-firing optical fiber is optically coupled to a source of laser energy and a metal tip, for reflecting laser energy laterally, is fixedly attached by crimping and/or an adhesive to the bared distal end of the optical fiber from which a portion of the protective buffer coating and any polymer cladding have first been removed. Optical fibers used in side firing devices typically have a 550 to 600 micron core diameter.

The metal tip is preferably made entirely of or coated with a material highly reflective to the wavelength of laser energy being used, such as silver or gold, stainless steel which has been plated with silver or gold, with a thickness of preferably at least five or more thousandths of an inch, stainless steel with an insert of gold or silver, preferably with a thickness of ten to twenty or more thousandths of an inch, or stainless steel coated with a dielectric.

Preferably, as described above, the protective buffer coating and any polymer cladding are removed from the distal end portion of the optical fiber prior to attachment of the metal tip. The metal tip can also be attached by an adhesive and/or crimping to the protective buffer coating covering the optical fiber, if desired. However, this is less desirable, as the metal tip may become heated and melt the plastic buffer coating, causing the metal tip to be dislodged, requiring a retrieval procedure.

The metal tip defines a central cavity, into which the distal end of the optical fiber extends. The distal end surface of the cavity is inclined at an angle of about 35° to 50°, preferably at an angle of about 45°. The open portion of the cavity allows laser energy, reflected by the inclined, reflective metal surface, to be emitted from the cavity in the metal tip at an angle of about 90° from the axis of the optical fiber, in accordance with Snell's Law.

For ease of manufacture and durability, the entire metal tip is preferably made of a highly reflective material, such as very pure gold or silver, both of which are easily malleable, preferably silver, which has about the same reflectivity as gold, but is much less expensive. Most preferably, the silver should be about 95.5% pure. For comparison, sterling silver is 92.5% pure.

In the device described above, the optical fiber is optically coupled to a source of laser energy and extends from the source of laser energy, through a longitudinal passageway or channel in a handpiece, for ease of use. A hollow liposuction cannula whose proximal end is fixedly attached within the distal end of the handpiece, is in fluid communication with the channel or passageway in the handpiece.

The inclined, reflective metal surface of the metal tip is disposed opposite a laser energy emission and fat entry port in the side wall of the liposuction cannula near its distal end. The length of the hollow. liposuction cannula depends upon the distance the liposuction cannula is desired to be inserted into the adipose tissue to be irradiated.

A hollow, male luer fitting, as known in the art, extends through the wall of the handpiece and is sealingly and fixedly attached and is in fluid communication with the channel in the handpiece. A suction tube from a vacuum or suction source with a female luer fitting at its distal end is attached over the male luer fitting of the handpiece to evacuate the liquefied fat, as known in the art. Alternatively, the handpiece may have a female luer fitting, and the suction tube may have a male luer fitting.

The optical fiber extends through the passageway and is fixedly attached to the handpiece, preferably within the proximal end of the handpiece by an adhesive or the like, which serves to sealingly close the proximal end of the passageway in the handpiece.

Alternatively the optical fiber may be removably attached within the proximal end of the handpiece by a compression fitting, as known in the art, which sealingly closes the proximal end of the handpiece. In addition to sealingly closing the distal end of the handpiece, the compression fitting, when loosened, enables the optical fiber and side firing device to be removed, cleaned and resterilized for use in another procedure, the handpiece and liposuction cannula to be cleaned, resterilized and used in another procedure and both to be cleaned, resterilized and used in another procedure, or either or both of them to be discarded.

The inside diameter of the hollow liposuction cannula is sufficiently larger than the outside diameter of the metal tip fixedly attached to the distal end of the optical fiber, to allow space for suction and fluid flow. The handpiece and the liposuction cannula may optionally be divided into two channels, each with its own luer fitting, one to introduce an irrigation liquid, such as sterile water or saline, to cool the tissue, and the other to allow the liquefied fat to be extracted by suction through the port, the hollow liposuction cannula, the passageway in the handpiece, the luer or other fitting and the suction tube, into a collection bottle. The irrigation liquid may optionally include a vasoconstrictor, an anesthetic and/or an antibiotic.

Alternatively, the liposuction cannula may be divided into two channels, one channel in fluid communication with the channel in the handpiece with the luer-fitting to a vacuum source, and the other channel with its own luer-fitting for infusion of an irrigating liquid, as described above, or vice versa.

If the liposuction cannula has only one channel, infusion of the irrigation liquid can be alternated with application of a vacuum or suction, or the infusion pressure of the irrigation liquid may slightly exceed the negative pressure of the suction or vacuum.

When laser energy is emitted, most of the blood vessels in the fatty tissue, which have been broken or cut during the liposuction procedure, are coagulated, reducing bleeding and the risk of infection.

The distal end of the liposuction cannula is closed ended and may have a blunt or rounded distal end, allowing it to pass through the skin through a surgically created opening. The distal end of the cannula may also be conical (pointed) or sharp, made with a double beveled needle-like shape or a trocar-like shape, which minimizes bleeding and hastens heating, as known in the art. However, maneuvering a sharp-ended device beneath the skin creates the risk of damaging unintended tissues, and requires extra care by the operator.

In another embodiment of the present invention, an optical fiber, optically coupled to a source of laser energy, from whose distal end portion the protective buffer coating and any polymer cladding has been removed, to produce an optical fiber with a "bared" distal end portion. The optical fiber extends through a hollow passageway extending lengthwise through the body of a handpiece. The optical fiber is fixedly attached to the handpiece, preferably within the proximal end of the handpiece, in a manner which sealingly closes the proximal end of the passageway, as described above.

A luer or other fitting, as known in the art, is sealingly and fixedly attached to and extends through the body of the handpiece and is in fluid communication with the hollow passageway. Alternatively, the optical fiber can be removeably attached within the proximal end of the handpiece with a compression nut or fitting, as known in the art, allowing the sterilization and re-use of either component or both, as described above.

A hollow metal or rigid plastic liposuction cannula, whose proximal end is in fluid communication with the passageway in the handpiece, is fixedly attached by an adhesive or the like within the distal end of the handpiece, as known in the art. The length of the liposuction cannula depends on the distance the cannula is desired to be inserted into the adipose tissue to irradiate it. The distal end of the optical fiber extends to a point about opposite a side opening or port near the distal end of the hollow cannula, which is closed-ended and rounded or blunt, but which may be pointed, sharp, syringe needle-shaped or trocar-shaped, whichever is desired.

After baring the distal end portion of the optical fiber, the distal end of the optical fiber is beveled at an angle of about 35° to 45°, preferably at an angle of about 38° to 44°, and most preferably at an angle of about 40° to 41°, which we have discovered produces optimal refection and laser energy transmission efficiency. To our knowledge, optical fibers used to create side firing devices for use in all other medical procedures are beveled at an angle of 35° to 37°, reflecting laser energy at an angle of 70° to 74°, according to Snell's Law. We tested optical fibers beveled in one degree increments and, contrary to common knowledge in the medical laser industry, found that a bevel angle of 40° to 41° produced optimal laser energy transmission efficiency, and that bevel angles less or greater than 40° to 41° resulted in lower energy transmission efficiency.

A closed-ended capillary tube is disposed over and fixedly and sealingly attached by an adhesive, thermal fusing, a combination of the foregoing or other means known in the art, to the bared distal end portion of the optical fiber. Fixedly and sealingly disposing a closed-ended capillary tube over the distal end of the optical fiber creates an air environment opposite the beveled, distal end surface of the optical fiber.

The difference in the refractive index of air, opposite the beveled, distal end of the optical fiber, versus the refractive index of the quartz or fused silica core of the optical fiber, enables total internal reflection of the light energy to occur laterally at an angle of double the bevel angle, according to Snell's Law. If the distal end of the optical fiber is beveled at an angle of 40° to 41°, laser energy is emitted at an angle of about 80° to 82° out of a side laser energy emission and fat entry port near the distal end of the hollow liposuction cannula opposite the beveled, distal end surface of the optical fiber, However, if a laser generating energy at wavelengths of about 1400 to 1500 nanometers (nm) or 1800 to 3000 mm, which wavelengths of light are highly absorbed by water, is emitted through an optical fiber, whose distal end has been most preferably beveled at an angle of about 40° to 41° for optimal reflection and laser energy transmission efficiency, in an aqueous liquid environment, we have found that the closed-ended capillary tube can be eliminated. The first portion of the laser energy emitted vaporizes a portion of the aqueous irrigation liquid infused through the liposuction cannula and creates a steam bubble to form opposite the beveled, distal end surface of the optical fiber.

The steam bubble has an index of refraction sufficiently lower than that of the refractive index of the quartz or fused silica core of the optical fiber to cause the laser energy to be reflected, according to Snell's Law, at an angle of about 80° to 82° out of the side port in the liposuction cannula, as described above.

However, an optical fiber with a low hydroxyl ion (water) content of about 0.1 to 100 parts per million ("ppm"), called a low-OH fiber, must be used with lasers whose wavelength is 1400 to 1500 or 1800 to about 2300 nm, to prevent excessive loss of laser energy. And, an optical fiber with an extremely low hydroxyl ion content of about 0.01 to 0.1 ppm, called an ultra low-OH fiber, must be used with lasers emitting energy at a wavelength of about 2300 to 3000 nm, to avoid excessive loss of laser energy at these wavelengths.

Laser energy at wavelengths of about 300 to 400 nm must be used through optical fibers with a high hydroxyl ion content of 600 to 800 ppm, called high OH fibers, to prevent excessive loss of laser energy at these wavelengths. Laser energy at wavelengths of about 400 to 1400 nm and about 1500 to 1800 nm can be used through conventional optical fibers with a hydroxyl ion content of 100 to 600 ppm or, preferably, for more efficient transmission efficiency, through or optical fibers with a low hydroxyl ion content, of about 0.1 to 100 ppm; to reduce transmission losses.

We have discovered that certain wavelengths of laser energy cannot be used through all of the three embodiments of the present invention described above.

Laser energy at wavelengths of about 1400 to 1500 nm and about 1800 to 3000 nm cannot be efficiently used through a side firing device in which an optical fiber whose distal end is opposed to an inclined surface of an attached reflective metal tip, as described above. Likewise laser energy of the above wavelengths also cannot be used through a side firing device in which the distal end of the optical fiber is beveled at an angle of 40° to 41°, without being fixedly encased within a closed-ended capillary tube.

In both such instances, an excessive amount of the laser energy will be wasted vaporizing the aqueous irrigation liquid, such as sterile water or saline used as an irrigating solution, between the distal end of the optical fiber and the reflective metal surface and between the reflective metal surface and the target tissue, or between the beveled, distal end surface of the optical fiber and the target tissue, leaving an insufficient amount of laser energy for effectively lysing fat cells and efficiently softening or liquefying the released fat.

Likewise, laser energy at wavelengths of about 300 to 1400 nm and about 1500 to 1800 nm cannot be efficiently used through a side firing device consisting of an optical fiber whose distal end has been beveled at an angle of about 35° to 45°, most preferably about 40° to 41°, with no closed-ended capillary tube sealingly encasing the distal end portion of the optical fiber, because no steam or gas bubble will be formed at the beveled distal end surface of the optical fiber, and no total internal reflection of the light energy will occur, as described above.

However, contrary to common wisdom in the medical laser field, we discovered that all wavelengths of laser energy from about 300 nm to 3000 nm, used through optical fibers with hydroxyl ion contents applicable to each, as described above, can be used through the second embodiment of the side firing devices described above, in which the distal end of the optical fiber is beveled at an angle of about 35° to 45°, most preferably at an angle of about 40° to 41°, and is fixedly and sealingly encased by a distally closed-ended capillary tube to create the air environment needed for total internal reflection of laser energy to occur.

A variety of lasers fall within wavelengths of about 300 nm to 3000 nm. For example, lasers emitting at 300 to 400 nm, include, for example, excited dimer lasers, called "eximer" lasers, including Xenon Chloride (XeCl) lasers emitting at a wavelength of about 308 nm and Xenon Fluoride (XeFl) lasers emitting at a wavelength of 351 nm, which wavelengths are highly absorbed by molecular bonds, causing disruption of tissue, including lysing of the membranes of fat cells, and softening or melting of the released fat.

Lasers emitting at 400 nm to 1400 nm and from 1500 nm to 1800 nm include, for example, an argon laser emitting at about 488 to 514 nm, a KTP laser emitting at a wavelength of 532 nm, which is highly absorbed by a red pigment, such as oxygenated hemoglobin in blood, a diode laser emitting at wavelengths of about 600 nm to 1400 nm, an alexandrite laser emitting at a wavelength of 810 nm, and a Nd:YAG laser emitting at a wavelength of 1064 nm, which wavelengths are absorbed to a modest extent by both pigments in blood and water, creating heat. These lasers have light extinction depths ranging from 800 to 4000 microns.

Lasers emitting at 1400 to 1500 nm and from 1800 to 3000 nm include, for example, a certain diode laser emitting at a wavelength of about 1470 nm, a Thulium:YAG laser emitting at a wavelength of about 2000 nm, a Chromium, Thulium, Holmium or CTH:YAG laser, commonly referred to as a "Holmium laser", emitting at a wavelength of about 2100 nm, a YSGG:YAG laser emitting at a wavelength of about 2106 nm. The aforementioned Thulium:YAG, CTH:YAG and YSGG:YAG lasers have light extinction depth in tissue of about 400 microns, and an Erbium:YAG laser emitting at a wavelength of about 2900 nm, whose light extinction depth in tissue is only about 50 microns, all of which wavelengths are highly absorbed by water, a constituent of all tissues, blood and the irrigation liquids commonly used in liposuction and endoscopic procedures.

According to Parlette, et al. in "Laser-Assisted Liposuction: Here's the Skinny" Seminars in Cutaneous Medicine and Surgery 27:259-263 (2008), laser energy at a wavelength of 924 nm from a diode laser has the highest absorption in fat, with low absorption in fibrous tissues with a high collagen content, causing less heating of and damage to such tissues. Such lasers may enable fat to be released, liquefied and evacuated with less vigorous suctioning.

Also, they advise that laser energy at a wavelength of 970 nm is well absorbed by collagen in fibrous tissue and, if the energy is controlled to produce tissue temperatures of about 48° to 50° C., tightening or shrinkage of the collagen in such tissue results. They suggest a combination of these wavelengths to produce both of the above described effects may be preferable.

They also advise that laser energy at a wavelength of 1,064 nm, from an Nd:YAG laser, has good tissue penetration, is well scattered by tissue and is poorly absorbed by fat, allowing greater heating of fatty tissues, and a diode or other laser emitting at a wavelength of 1,320 nm offers a combination of greater fat absorption, less tissue penetration and less scattering than laser energy at a wavelength of 1,064 nm. They suggest a combination of these wavelengths may be synergistic.

They mention that laser energy at wavelengths highly absorbed by lipid-rich tissues can be used to selectively heat fat cells, rupturing their fragile membranes and releasing their contents, with less risk of damage to other tissues.

They also report lysing of the membranes of fat cells and liquefaction of fat occurs when laser energy causes tissue temperatures of about 40° to 45° C. Denaturization of structural proteins also occurs at these temperatures, which may stimulate collagen remodeling and tissue tightening. They also state that fat has a water content of 14% and collagen has a water content of 60% to 70%.

U.S. Pat. No. 7,060,061 B2, by Altshuler G B et al, states that fat absorbs light at bands between (a) 880 and 935 nm, (b) 1150 and 1230 nm, (c) 1690 to 1780 nm or (d) 2250 to 2450 nm. Lasers emitting between 900 to 930 nm, such as a Gallium Arsenide laser emitting at 920 nm, or between 1200 to 1230 nm, such as a lamp pumped, solid state laser crystal doped with Erbium$^{+3}$ ions emitting at 1200 nm, are preferred, as they are not highly absorbed by water, a significant constituent of skin and other tissues. Lasers emitting at 2250 to 2450 nm include lasers such as a $Cr^{2+}$:ZuSe or $Cr^{2+}$:ZnS laser, as well as a $Tm^{3+}$ doped fluoride or $Ho^{3+}$ doped fluoride laser.

Neither mentions the use of laser energy at wavelengths of 1800 to 2200, which include Thulium:YAG, CTH:YAG and YSGG:YAG lasers and others, of which CTH:YAG lasers provide laser energy in pulses typically of 250 to 350 microseconds in duration. At a pulse repetition rate of 10 pulses per second, a second consists of ten segments of 100,000 microseconds each. After each 250 or 350 microsecond pulse, there are 99,650 to 99,750 microseconds for the tissue to cool.

This is a ratio of cooling time to laser energy emission time of 185:1 Even at a pulse repetition rate of 20 pulses per second, the ratio of cooling to laser energy emission is about 142:1.

The above lasers, all known in the art, and others, can be used in laser liposuction procedures, laser lipolysis procedures followed by liposuction or laser lipolysis procedures alone, with the devices and in the manner described herein.

With such a range of wavelengths of laser energy available, with few if any comparative published studies, clinicians must rely upon their experience in using various wavelengths of laser energy in fat removal procedures in which they have performed well.

A vacuum pump or other suction source can be attached to a collection bottle by a vacuum line or tube, and the collection bottle can be separately connected to a suction tube attached to and in fluid communication with the luer or other fitting in fluid communication with the passageway in the handpiece. Suction can be applied to draw the softened or liquefied fat through the side port in the cannula, through the liposuction cannula and either (a) the passageway in the handpiece and the luer or other fitting and (b) through a separate luer-fitting in fluid communication with a separate suction channel in the liposuction cannula and, in either case, ultimately into the collection bottle, as known in the art.

The handpiece can have a raised button, whose color may be significantly different from that of the handpiece, which the operator can see and sense by tactile feel, as known in the art. The button can be positioned on the side of the handpiece from which the laser energy is emitted or, preferably, on the side of the handpiece opposite the side from which the laser energy is emitted. If so positioned, when the handpiece is gripped, the forefinger or thumb of the operator, touching the button, points in the direction in which the laser energy will be emitted, as known in the art.

An aiming beam of a desired color, for example, red or green, such as from a helium neon (HeNe), a light emitting diode (LED), a diode laser or other laser emitting about 1 to 5 milliwatts of energy can be transmitted through the optical fiber and reflected at about the same angle as the therapeutic laser energy to enable the operator to see, through the skin, the direction in which the therapeutic laser energy is being emitted. Green may be preferred, as red may be more difficult to discern in an area containing blood.

The unique construction of any of the three, side firing devices described above, and other constructions known in the art, whether fixedly disposed within a liposuction cannula or not, may be employed to uniformly lyse the membranes of fat cells and soften or liquefy the released fat. These devices can also be used in a novel method of use to achieve a significantly more effective, safe and uniform fat removal and tissue vaporization effect, as described below.

The key to the safe use of laser energy emitted laterally at an angle of 70° to 90° from the axis of an optical fiber in a fat cell lysing and fat liquefaction procedure, concurrently with, followed by or without a liposuction procedure, is to avoid laser energy being emitted (a) at or near 12 o'clock, toward the dermis of the skin, which can cause tissue damage, discoloration and/or coagulation of blood vessels that nourish the dermis or (b) at or near 6 o'clock, toward deeper body tissues, which could damage and/or coagulate blood vessels, nerves or other delicate internal body structures that are not intended to be exposed to laser energy during the fat removal procedure.

After insertion of the side firing device, whether contained in or followed by the insertion of a liposuction cannula or not, through a surgically created opening in the skin (or an opening created by a sharp or pointed tip, a double-beveled needle or trocar-like tip), the side firing device is advanced into the fatty tissue beneath the dermis, lateral to the surface of the skin, with the surface of the skin being 12 o'clock. The button on the handpiece can be positioned, for example, at 9 o'clock, causing laser energy to be emitted at 3 o'clock, or the button can be positioned, for example, at 3 o'clock, causing laser energy to be emitted at 9 o'clock.

While the side firing device removably attached within a liposuction cannula by a compression fitting or nut, as described above, is advanced and/or withdrawn, laser energy can be emitted, depending on the wavelength of laser energy being used, at a power level of about 2 to 30 watts, preferably about 5 to 20 watts, with greater power applied for faster movement of the cannula, provided the laser energy emission is accompanied by the infusion of a sterile water or saline or a spray of sterile water or saline to cool the tissue.

When the side firing device is used through a liposuction cannula with infusion of a sterile irrigating fluid, the button on the handpiece can be positioned at 9 o'clock and laser energy may be emitted for about 5 to 30 seconds at 3 o'clock, while repetitively rotating the liposuction cannula (or the side firing device, if used by itself), cannula through an arc of up to 120°, from up to about 1 to 5 o'clock, as the liposuction cannula (or the side firing device if used by itself) is being withdrawn and advanced, preferably for about 2 to 5 seconds in each direction, depending upon the length of the liposuction cannula (or the side firing device) and the distance it is to be extended into the body, the thickness of the fatty tissue layer and the rate of advancement or withdrawal, as determined by the physician performing the fat removal procedure. Then, the button can be positioned at 3 o'clock and the above described laser energy emission procedure can be repeated at 9 o'clock, while advancing and withdrawing and repetitively rotating the liposuction cannula back and forth through an arc of up to about 120°, from up to about 7 to 11 o'clock.

For example, if the length of the liposuction cannula is about 30 cm, the distance the cannula is extended into the body beneath and parallel to the surface of the skin is typically about 25 to 28 cm, the laser energy level, the period of laser energy emission and the advance and withdrawal rate of the cannula may be proportionately increased or reduced at the discretion of the physician. If a pulsed or gated laser energy source is used, the pulse duration and/or repetition rate may also likewise be proportionately increased or reduced, based on the above parameters In a preferred method of use, the button on the handpiece is positioned at 9 o'clock, and laser energy is emitted at 3 o'clock. The liposuction cannula may be moved from its furthermost, position to near the insertion point, and back to its furthermost position, at a rate of about 1 to 5 cm per second, preferably at about 2 to 3 cm per second, while it is repetitively rotated through an arc of up to about 120° from up to about 1 to 5 o'clock, as described above, at the rate of about one cycle about each 0.5 to 2 seconds, preferably about one cycle about each second, enabling the operator to time each arc while mentally counting one thousand, two thousand, etc.

Thereafter, the withdrawal and advancement of the liposuction cannula is repetitively repeated until little or no fat is seen to enter the collection bottle. The size of the arc, the rate of advancement and withdrawal and the rate of rotation of the liposuction cannula may be proportionately increased or decreased by the physician, based on the parameters described above.

The above procedure is then repeated, with the button of the handpiece positioned at 3 o'clock and laser energy being emitted at 9 o'clock, at the power levels and for the time periods described above, while advancing and withdrawing the liposuction cannula and repetitively rotating it through an arc of up to about 120° from up to about 7 to 11 o'clock, as described above.

Looking at the laser energy emission pattern, head-on from the distal end of the side firing device, the laser energy emission pattern has a "bowtie" cross-sectional shape. This results in lysing the membranes of a larger number of fat cells, allows the softening or liquefying of a greater volume of the released fat and enables the removal of a larger amount of fat than is possible from the use of a straight ahead-firing optical fiber over the same range of linear motion, and also results in a more uniform fat liquefaction and removal process, without exposing the dermis at about 12 o'clock or deeper tissues at about 6 o'clock to unintended laser energy.

Instead of advancing and withdrawing the liposuction cannula, in a preferred method of use, deeper and wider liquefaction of the fatty tissue can be achieved by positioning the distal end portion of the liposuction cannula at a series of selected positions, each about 0.5 to 2 cm apart, preferably about 1 cm apart. This process may be started with the distal end portion of the liposuction cannula near its furthermost advancement point, or near its insertion point, preferably near its furthermost point.

Laser energy is emitted at 3 o'clock, while the liposuction cannula is rotated through an arc of up to about 120°, for example, from up to about 1 to 5 o'clock, as described above, at the starting selected position for a desired rate of rotation, period of time and laser energy level described above. This process is then repeated, with laser energy being emitted at 9 o'clock, while the liposuction cannula is repetitively rotated through an arc of up to about 120°, from up to about 7 to 11 o'clock, for the rate of rotation, period of time and laser energy level described above.

Then, the liposuction cannula is withdrawn or advanced in a series of steps to other selected positions, each about 0.5 to 2 cm apart, preferably about 1 cm apart, and laser energy is again emitted at each of said selected positions, while rotating the liposuction cannula therapy an arc of about 120°, from up to about 1 to 5 o'clock and, then, from up to about 7 to 11 o'clock, and rotated as described above, for a desired period of time, laser energy level and rotation rate, as described above.

Depending upon the length of the layer of adipose (fatty) tissue, at the discretion of the physician, the above described positionings and emissions of laser energy may be repeated until the liposuction cannula is withdrawn to up to about two cm from its insertion point into the body. Alternatively, these positionings may begin one or two cm or more from the insertion point and continued through a series of positionings to the liposuction cannula's furthermost position, or vice versa.

The above described series of laser energy emissions and repetitive rotations of the liposuction cannula at a series of selected positions, as described above, achieves two benefits. First, the laser energy has time to penetrate the fatty tissue to its light extinction depth, which is dependent upon the wavelength of laser energy being used and its light extinction depth in the tissue being treated.

Second, since the liposuction cannula is not continuously moving back and forth as laser energy is being emitted, this allows time for greater thermal diffusion or propagation of heat, from the laser energy's light extinction depth, farther into the fatty tissue. This increases the total depth and width of the bowtie-shaped, fat cell lysing and fat liquefaction pattern, increasing both the depth and width of the fat cell lysing, fat liquefaction and evacuation process.

In a most preferred fat removal process, the two above-described procedures are combined. For example, in the first procedure, laser energy is emitted in a series of steps at selected positions from the furthermost point of the liposuction cannula to near its insertion point, with the liposuction cannula being repetitively rotated as described above at each position, after which the liposuction cannula is advanced in a series of steps at selected positions to its furthermost position, as described above.

Thereafter, in the second procedure, the liposuction cannula oriented to emit laser energy in a desired direction, for example at 3 or 9 o'clock, is positioned at a series of points or is slowly advanced and withdrawn at a desired rate and, while a desired level of laser energy is emitted, the liposuction cannula is repetitively rotated as described above. Any of the above described elements can precede the other.

A greater volume of fat can be liquefied and evacuated in the first procedure, emitting laser energy in a series of steps at selected positions, which allows time for thermal diffusion of the laser energy to occur. However, recalling the "bowtie" pattern described above, the narrow beam of laser energy emission near the laser energy emission point out of the side port of the liposuction cannula) leaves areas of fatty tissue not lysed, melted or liquefied immediately to the left and right of the laser energy emission port of the liposuction cannula, as is readily apparent in FIGS. 6 and 7.

This is corrected during the second procedure, in which the liposuction cannula is slowly advanced and withdrawn, while emitting laser energy and repetitively rotating the liposuction cannula through an arc of about 120°, as described above, lysing the fat cells missed by the first procedure and softening or liquefying the released fat. The combination of these procedures produces a more uniform removal of a greater volume of fat for a more pleasing cosmetic effect, as is readily apparent in FIG. 9.

Alternatively, to achieve a similar effect on fat cells not lysed and released fat not softened or liquefied to the left and right of the laser emission point when the liposuction cannula is positioned and laser energy is emitted in a series of steps at selected positions for the time periods, laser energy levels and rotation rate described above, the liposuction cannula can be slowly moved back and forth between one selected lasing position and the next selected lasing position, while laser energy is emitted first at 3 o'clock and then at 9 o'clock, or vice versa, while repetitively rotating the side firing device through an arc of up to about 120°, from up to about 1 to 5 o'clock and then from up to about 7 to 11 o'clock, respectively, for the time periods, the laser energy levels, the advancement and withdrawal rate and the rotation rate described above.

In an alternate embodiment of the side firing device of the present invention, the inclined reflective surface at the distal end of the cavity in the metal tip, or the beveled, distal end surface of the optical fiber of the second or third embodiment of the present invention, can each be vertically beveled into a chisel-like shape, reflecting the laser energy simultaneously at 3 o'clock and 9 o'clock. If such a side firing device is fixedly disposed within a liposuction cannula, the liposuction cannula must have two ports, each positioned opposite the inclined or beveled, laser energy emitting surfaces of the side firing device. This avoids having to first orient the side firing device to emit laser energy at about 3 o'clock and then reposition the side firing device to emit laser energy at about 9 o'clock.

If, for example, 20 watts of laser energy from a KTP laser at 532 nm, a diode laser at 980 nm or a Holmium laser at 2100 nm, is emitted from a side firing device whose core diameter is 550 microns and whose numerical aperture or "NA" is 0.22, the energy density or fluence of the laser energy beam from the laser energy emission point over a period of one second would be about 4,000 joules per square centimeter for any of these wavelengths.

In a more preferred embodiment of the present invention, as is more amply detailed in the discussion of the drawings, we discovered that the beveled, distal end surface of the optical fiber may be encased within a closed-ended capillary tube with a substantially thinner wall thickness, which causes the laser energy to be more widely diverged, enabling a greater volume of fat cells to be lysed and a greater volume of released fat to be softened or liquefied and extracted, and allows the side firing device to be rotated through an arc of only about 90° to achieve the same effect. In this embodiment, the wall thickness of the capillary tube is not greater than 350 microns, compared to a wall thickness of about 500 microns of the capillary tube in the above-described second and third embodiments of the present invention.

In another more preferred embodiment of the present invention, to center the optical fiber in the liposuction cannula, the cannula is extruded with ribs extending from the inner surface of the liposuction cannula into the channel of the cannula to a distance sufficient to sealingly contact the exterior of the optical fiber. Any number of ribs can be used, but at least three ribs are preferred to stabilize the optical fiber within the center of the liposuction cannula.

However, the ribs must not extend into the area of laser energy emission through the port or ports in the liposuction cannula, and, the ribs should preferably terminate proximal to said ports. Of course, any greater number of ribs may be employed to keep the optical fiber centered in the liposuction cannula.

Alternatively, the liposuction cannula can be extruded with one wall within the other, with at least two ribs, preferably three or more, to hold the outer wall a desired distance from the inner wall, whose I.D. is sufficient to admit the side firing device.

In most conventional liposuction procedures, a liquid containing an anesthetic, preferably along with a vasoconstrictor and/or an antibiotic to prevent infections, is infused through the liposuction cannula. Infusing such a liquid during a liposuction procedure is called "tumescent" liposuction. The infusion of such a liquid may force apart or cause layers of tissue and fat to constrict and separate, resulting in a less traumatic and greater fat removal volume in an overall safer fat removal procedure. Such liquid may be infused through the space between at least two ribs, while suction is applied to the spaces between the other ribs, at a pressure exceeding by a small margin the negative suction pressure.

In yet another more preferred embodiment, at least one of the ribs in the liposuction cannula has a central channel, which may be round, elliptical or of any other shape, through which a liquid containing an anesthetic, preferably with a vasoconstrictor and/or an antibiotic, can be infused, at a pressure somewhat greater than the negative pressure used to evacuate the liquefied fat.

Infusion of the anesthetic or anesthetic-vasoconstrictor combination, with or without an antibiotic, can be introduced through a separate luer or other fitting into a separate compartment (not separately shown) in the handpiece, which compartment is in fluid communication with the spaces between at least two of the ribs, through a separate channel in the liposuction cannula with its own luer fitting or through a channel in at least one of the ribs, as known in the art, using a manually-operated syringe or mechanical syringe pump to create the desired pressure, as known in the art.

When the operator steps on the foot switch to actuate the laser, optionally, the vacuum pump or other suction source may also be actuated by the same foot switch.

The three side firing optical fiber device embodiments described above can also be used by themselves, followed promptly by the use of a liposuction cannula to remove the softened or liquefied fat, or simply by themselves, without utilizing a liposuction cannula during or after the fat cell lysing and liquefaction procedure, allowing the softened or liquefied fat to be absorbed into the bloodstream and transported to the liver and/or intestines, where it may be metabolized, as described above.

However, there is conflicting data on the effect of laser energy to lyse fat cells and liquefy the released fat being promptly followed by a liposuction procedure or being left to be absorbed into the bloodstream. As indicated by Parlette, et al. (op. cit.) there is little evidence of an increase in circulating triglycerides or cholesterol after laser lipolysis alone. And, there is a risk to liver and kidney function if triglycerides and free fatty acids are not concurrently or quickly removed by conventional liposuction after laser lipolysis.

If any of the three side firing devices described above are used alone, and are not used in a liposuction cannula or not promptly followed by the use of a liposuction cannula, it may be desirable to confine their use to small areas of the body with small fat deposits, such as in the face and around the eyes, until comparative studies to prove the safety of their use alone are available.

The use of laser energy in lysing of fat cells and liquefaction of the released fat produces a significant additional benefit. Laser energy causes the photomechanical cross-linking of collagen, which reduces its volume. In our laboratory testing, in a water bath, when strips of cartilage, which has a very high collagen content, were exposed to laser energy, their length was shrunk by about 30%, if not under stress. If under stress, when exposed to same level of laser energy, the shrinkage of strips of cartilage in a water bath was about 10% in length.

Skin has a relatively high collagen content, albeit not as high as that of cartilage. Laser energy causes modest shrinkage of the epidermis and greater shrinkage of the dermis, which is closer to the source of laser energy emission. This results in the smoothing of wrinkles and tightening of the skin, reducing its sagging after the removal or absorption of the liquefied fat.

Of the various wavelengths of laser energy which create the photomechanical cross-linking of collagen, CTH:YAG or Holmium laser energy is preferred, as it is pulsed and allows the tissue to cool between pulses, as described above, reducing or eliminating charring which can discolor the skin and lengthen the healing process.

If the side firing device is used by itself and is not intended to be followed by a liposuction procedure to remove the liquefied fat, we have developed a unique handpiece that provides a space sufficiently large to accommodate the operator's fingers, enabling the side firing device, contained within a rigid plastic or metal sheath, preferably medical grade stainless steel, to be inserted beneath the skin and kept parallel to the surface of the skin.

If space for the operator's hand or fingers is not provided, the side firing device tends to be inserted at a downward angle and, as it is advanced, will move too deeply below the adipose tissue layer, endangering underlying blood vessels, nerves or other tissues.

To construct this handpiece, the optical fiber of the side firing device must be sufficiently flexible to pass through two 90° bends of a small radius. Optical fibers leak laser energy if the radius exceeds 1 cm and the core of the optical fiber exceeds 200 microns.

As a result, in addition to the unique handpiece, a side firing device (a) using a smaller diameter core than used in any other side firing device ever marketed and (b) which is capable of transmitting at least 30 watts of laser energy, preferably from a diode or CTH:YAG laser is utilized. As a rule, the smaller the core diameter of an optical fiber the more difficult it is to efficiently focus laser into it without a sizable loss of laser energy.

In addition, the optical fiber must have a numerical aperture or "NA" of 0.22, which is commonly used in medical devices and is available at a low cost, versus special runs of optical fibers with a different na.

In addition to traversing the two 90° bends, the side firing device must have a small diameter to enable it to be inserted through a very small surgically created puncture or must have a sharp distal end to create its entry point which, as mentioned above, requires extra care by the operator.

We solved this problem, as seen in FIG. 15, below, by constructing the smallest diameter side firing device ever commercialized, with an O.D. of only 1.5 mm (commonly available side firing devices have O.D.s of 200 mm or larger). This "mini" side firing device utilizes an optical fiber with a core diameter of only 365 microns, one-third smaller in core diameter than a conventional 550 micron core diameter optical fiber, yet it is able to efficiently convey, contrary to accepted wisdom in the medical laser field, up to 50 or more watts of CTH:YAG laser energy without significant loss.

The capillary tube that fixedly and sealingly encases the bared and distally beveled end surface of the 365 micron core diameter optical fiber, to provide the air interface necessary for total internal reflection of the laser energy at an angle of 80° to 82° from the axis of the optical fiber, has a wall thickness of 350 microns for use at low levels of laser energy (0.1 to 3 watts) or 500 microns for use at high levels of laser energy (20 to 100 watts), and is snugly fitted over the bared, beveled distal end portion of the optical fiber, with a gap not exceeding 25 microns (one thousandth of an inch).

The capillary tube is attached to the bared optical fiber near its proximal end by an adhesive, preferably an adhesive with a high melting point and which is substantially transparent to the CTH:YAG laser's 2100 nm wavelength of light, as well as those from most other lasers commonly used in medical procedures. For added security, the junction of the proximal end portion of the capillary tube and the optical fiber's protective buffer coating is covered by a shrink wrapping material, which is attached with the same adhesive.

A suitable adhesive for this purpose is an optically transparent, low viscosity epoxy adhesive with a high melting point, such as a U.S.P. Class VI approved, two-component epoxide epoxy resin. As a result, even exposed to stray laser energy emitted backward from imperfections in the distal, beveled end surface of the optical fiber and the interior of the capillary tube, the adhesive is not heated to near its melting point, when fully hardened or set.

The irrigation fluid, such as sterile water or saline, which may contain an anesthetic, vasoconstrictor and/or an antibiotic, is infused to cool the tissue and the capillary tube/optical fiber assembly, allowing a higher level of laser energy to be used, for example, up to 30 watts. A hollow tube or sleeve of a plastic, such as polyether ether ketone (PEEK), can be provided enclosing the optical fiber from within the distal end of the handpiece in fluid communication with the lengthwise channel of the handpiece, up to the proximal end of the capillary tube. The irrigation liquid, as described above, may be infused through a separate luer fitting attached to and in fluid communication with the plastic sleeve distally from the distal end of the handpiece, or through a luer fitting attached to the handpiece in fluid communication with the lengthwise channel in the handpiece and the plastic sleeve.

If it is desired to infuse irrigation liquid separately from the anesthetic, vasoconstrictor and/or antibiotic, the plastic sleeve can be constructed with two lumens, each in fluid communication with a dedicated luer fitting.

This smaller diameter side firing device is particularly desirable for use in procedures in the face, particularly around the eyes, and under the skin of the neck.

Other variations of side firing devices for laser fat lysing, softening or liquefying fat and its removal or absorption can be made without departing from the principles set forth herein and without limiting the intent and scope of the present invention.

The above-described devices can be used in the above-described manner for the same purpose in another tissue application, using the bowtie-like laser energy vaporization pattern to vaporize excess nucleus pulposus tissue of a spinal disc, causing a bulge or herniation in the disc to occur. The annulus or outer protective ring of tissue, surrounding the nucleus pulposus, to be stretched and pressed against nerve encircling the disc, resulting in incessant pain.

BRIEF DESCRIPTION OF THE DRAWINGS

FIG. 1 is an external, side view of the device suitable for practicing the present invention, with an expanded, sectional, side view of the distal end portion of the optical fiber.

FIG. 2 is a cross-sectional, side view of another embodiment of the distal end portion of the optical fiber.

DETAILED DESCRIPTION OF THE INVENTION

Figure 3:
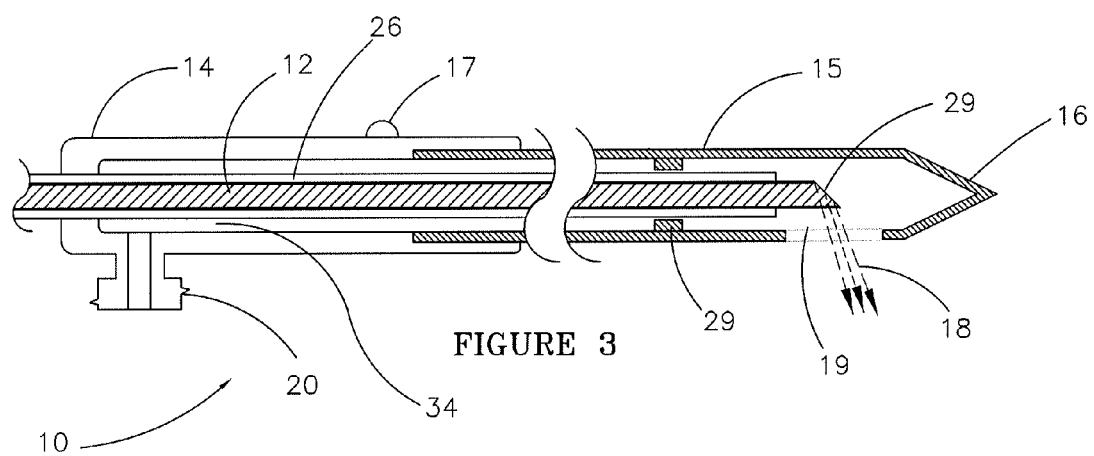
FIG. 3 is a sectional, side view of the distal end portion of another embodiment of the distal end portion of the optical fiber.

As illustrated in FIG. 1, device 10 is comprised of laser energy source 11 and optical fiber 12, whose proximal end is fixedly encased in connector 13, which optically couples optical fiber 12 to laser energy source 11. Optical fiber 12 is fixedly and sealingly attached within the proximal end of handpiece 14, as known in the art, and extends through a hollow passageway or channel (not separately shown) in handpiece 14, which extends lengthwise through handpiece 14, and is in fluid communication with hollow liposuction cannula 15. Alternatively, optical fiber 12 may be removeably and sealingly attached within the proximal end of handpiece 14 by a compression fitting (not separately shown), as known in the art.

The distal end 16 of cannula 15, as shown in FIG. 1, is rounded. Distal end 16 of cannula 15 may also be blunt, sharp, double-bevel needle shaped, trocar shaped or of any other desired shape, as known in the art.

Button 17 on handpiece 14, in this embodiment, is preferably positioned on the side of handpiece 14 opposite the side of handpiece 14 from which the emission of laser energy occurs, as shown by arrows 18, through laser energy emission and fat entry port 19 in cannula 15. While button 17 may also be positioned on the side of handpiece 14 from which the emission of laser energy 18 occurs through port 19 in cannula 15, button 17 will be less able to be visualized during use.

Luer or other connector fitting 20, which is fixedly attached within and extends through the wall of handpiece 14, is in fluid communication with the passageway (not separately shown) in handpiece 14, cannula 15 and port 19. Vacuum pump 21 creates suction through vacuum tube or line 22 to collection bottle 23, which has fluid volume markings 24 on its exterior. Collection bottle 23 is separately in fluid communication through suction tube or line 25 to luer or other port 20, the hollow passageway (not separately shown) in handpiece 14, hollow liposuction cannula 15 and port 19.

As shown in the cut-through, expanded view of the distal end portion of device 10, buffer coating 26 of optical fiber 12 has been removed from the distal end portion of optical fiber 12, which extends into a cavity in metal tip 27 which is fixedly attached to the bared distal end portion of optical fiber 12 by an adhesive, crimping or both, or by other means known in the art (not separately shown). As illustrated, the cavity in metal tip 27 is formed with a reflective, inclined surface 28 opposite the distal end face of optical fiber 12. Reflective surface 28 of metal tip 27 is inclined at an angle of about 35° to 50°, preferably about 45°, to reflect the laser energy from inclined reflective surface 28 at an angle of about 90° from the axis of optical fiber 12, as shown by arrows 18, out of emission port 19 in liposuction cannula 15.

Metal tip 27 can be made entirely of a metal highly reflective to the wavelength of laser energy to be used, such as gold or silver, or metal tip 27 can be made of a material such as medical grade stainless steel, which is plated with a highly reflective metal, such as gold or silver with a thickness of about 5 thousandths of an inch or more, or coated with a dielectric highly reflective to the wavelength of laser energy to be used, as known in the art. Alternatively, an insert with a thickness of about 10 to 20 thousandths of an inch or more of a metal highly reflective to the wavelength of laser energy being used, such as gold or silver, may be force-fitted or attached by an adhesive, or both, in a recess in the distal end of the cavity in metal tip 27.

Polished copper, brass, aluminum or stainless steel, which cost less than gold or silver, may also be used. However, stainless steel is not a highly efficient reflector, and copper and aluminum are not as reflective as gold or silver and are subject to tarnish and/or oxidation, which reduces their reflectivity.

95.5% pure Silver is about 97% reflective at wavelengths of about 500 to 2400 nm, and about 95.5% reflective at 430 nm. 95.5% pure Gold is less than 50% reflective below wavelengths of 500 nm, 81.7% reflective at 550 nm, 91.9% reflective at 600 nm, 95.5% reflective at 650 nm and about 97% reflective at 700 nm and longer wavelengths. 75.5% pure platinum is extremely expensive and is only 71.4% to 81.8% reflective at wavelengths of 500 to 2000 nm and is 88.8% reflective at 3000 nm. Very pure silver is preferred, because it is highly reflective and is considerably less expensive than gold or platinum.

For greater durability, a lower cost of manufacture and resistance to erosion by the emission of laser energy, metal tip 27 is preferably made entirely of very pure gold or silver, preferably of very pure silver with a purity of about 95.5% (for comparison, "sterling" silver is 92.5% pure).

As shown in FIG. 2, distal end 16 of hollow cannula 15 is shaped like the distal end of a double beveled syringe needle, which cuts rather than making a puncture or hole through the skin, reducing bleeding and the risk of an infection. To prevent tissue from lodging in the opening at the distal end of cannula 15, plug 30 of an adhesive or other material, preferably heat resistant to any stray laser energy, or a highly reflective material as described above, may be used to fill the distal end of cannula 15.

Using a sharp-ended cannula beneath the skin entails considerable risk to the patient and requires greater care by the operator. Preferably, distal end 16 of hollow cannula should be blunt or rounded if a large area of the body is to be treated with multiple insertions, advancements and withdrawals of device 10.

Buffer coating 26 has been removed from the distal end portion of optical fiber 12, and the distal end of optical fiber 12 has been ground and polished into beveled, distal end surface 29 at an angle of about 35° to 45°, preferably at an angle of about 40° to 41°, which we have found by testing various bevel angles at 1° intervals, to be the most efficient bevel angle for total internal reflection of laser energy at relatively high power levels.

If the beveled, distal end surface 29 of optical fiber 12 is ground and polished at an angle less than 40°, the laser energy will be less optimally reflected and more scattering of laser energy will occur. If the distal end of optical fiber 12 is beveled at an angle of 82° or greater, the transmission of laser energy will be substantially lower.

The proximal end portion of closed-ended capillary tube 31 may be sealingly attached to the bared distal end portion of optical fiber 12 by thermal fusion (not separately shown) and/or adhesive 31, neither which extends into the area of laser energy emission from beveled surface 29 of optical fiber 12. If capillary tube 31 is thermally fused to bared optical fiber 12 near or at beveled distal end surface 29, beveled surface 29 may melt and lose its flatness, reducing its laser energy transmission efficiency.

Capillary tube 31 defines air pocket 32 opposite beveled, distal end surface 29 of optical fiber 12. The refractive index of air pocket 39 is substantially lower than the refractive index of the core of optical fiber 12, and enables total internal reflection of the laser energy to occur, according to Snell's Law, at an angle of about 80° to 82° from the axis of optical fiber 12, as shown by arrows 18, out of port 19 in cannula 15 opposite distal beveled end surface 29 of optical fiber 12. Total internal reflection of light is often referred to as "TIR" or "refraction".

FIG. 3 illustrates an alternate embodiment of device 10 of FIG. 2, in which no capillary tube is utilized to encase the beveled, distal end surface 29 of optical fiber 12. As a result, no air pocket is created opposite the beveled surface of optical fiber 12. As shown, distal end 16 of cannula 15 is pointed or conically shaped. As mentioned above, the use of a pointed or sharp-ended cannula beneath the skin entails significant risk and requires greater care by the operator.

In this embodiment, if laser energy at a wavelength of 1400 to 1500 nm or 1800 to 3,000 nm, which wavelengths of light are highly absorbed by an aqueous liquid, such as saline or sterile water used in liposuction procedures or as an irrigation fluid in endoscopic procedures, is used at ten or more watts of power, such wavelengths of laser energy cause a steam and/or gas bubble (not separately shown) to form with each pulse of laser energy opposite beveled distal end surface 29 of optical fiber 12, from the vaporization of the aqueous irrigation liquid, blood, body fluids and/or tissue, through which the balance of the pulse of laser energy passes to the target tissue.

The refractive index of the steam and/or gas bubble opposite beveled, distal end surface 29 of optical fiber 12 is sufficiently lower than that of the quartz or fused silica core of optical fiber 12 to enable the laser energy to be totally internally reflected from beveled distal end surface 29 of optical fiber 12, laterally from the axis of optical fiber 12 at an angle of 80° to 82°, according to Snell's Law, without requiring the use of a capillary tube over the 41° to 42° beveled, distal end surface 29 of optical fiber 12 to create an air interface. This saves the cost of the capillary tube, closing its distal end and fixedly attaching its proximal end portion to bared optical fiber 12.

Figure 4:
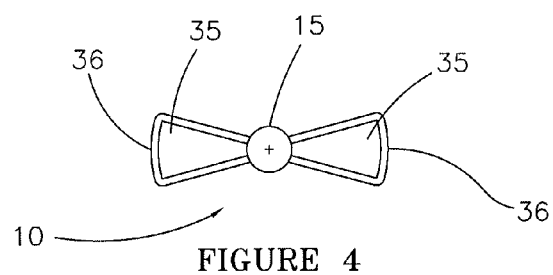
FIG. 4 is a graphical representation of an end view of the laser energy emission and fat liquefaction pattern of a method of use of the devices of FIGS. 1-3.

As illustrated in FIG. 4, laser energy emission pattern shown from a head-on or distal end view of optical fiber 12, as a result of laser energy being emitted at three o'clock and then at 9 o'clock, while rotating optical fiber 12, handpiece 14, cannula 15 and emission port 19 through an arc of up to about 120°, as described above, from about 1 to 5 o'clock and then from about 7 to 11 o'clock, respectively. This creates bowtie-shaped laser energy emission area 35 and thermal diffusion area 36, which is larger than laser energy emission area 35 due to the thermal diffusion or propagation of heat into the fat layer.

The benefit of producing a bowtie-shaped laser energy emission area 35 and larger thermal diffusion area 36 is a greater volume of fat cells are lysed and a larger volume of released fat can be softened or liquefied by a side firing device than by a conventional, straight ahead-firing optical fiber, while avoiding thermal damage to or discoloration of the dermis or coagulation of blood vessels nourishing the dermis (not separately shown) at or near 12 o'clock, and damage to deeper structures, including blood vessels, nerves and other tissues (not separately shown) at or near 6 o'clock.

Figure 5:
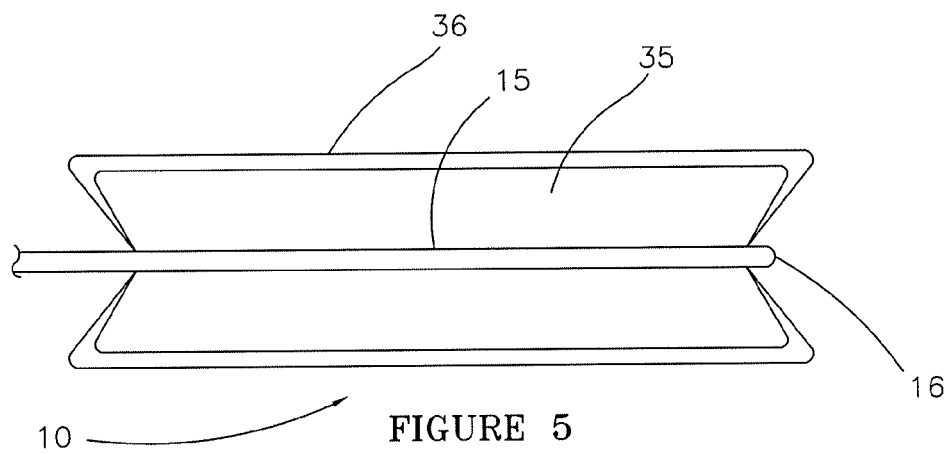
FIG. 5 is a graphical representation of a top view of the laser energy emission and fat liquefaction pattern from one method of use of the devices of FIGS. 1-3.

FIG. 5, looking from above the skin, illustrates the laser energy emission area 35 and thermal diffusion area 36 of device 10, as handpiece 14, liposuction cannula 15 and laser energy emission port 19 are positioned at 3 o'clock and slowly advanced and withdrawn through a fatty layer beneath the skin, at the rate described above. while laser energy is emitted at power levels and for the time periods described above, and handpiece 14 is repetitively rotated or cycled through an arc of about 120°, from about 1 to 5 o'clock, after which the procedure is repeated with emission port 19 positioned at 9 o'clock and, while laser energy is emitted, side firing device 10 is repetitively rotated or cycled through an arc of about 120° from about 7 o'clock to 11 o'clock, as described above. Either of these positionings of port 19 at 3 o'clock or 9 o'clock can precede the other.

Thermal diffusion area 36 is larger than that of laser energy emission area 35, due to thermal diffusion or propogation of heat through the tissue, enabling a larger volume of fat cells to be lysed and a greater volume of released fat to be softened or liquefied. Laser energy emission area 35 and thermal diffusion area 36 are substantially larger than that which could be obtained with insertions at multiple angles and passes, back and forth of a conventional, liposuction cannula containing a straight ahead-firing optical fiber disposed within a conventional liposuction cannula.

Figure 6:
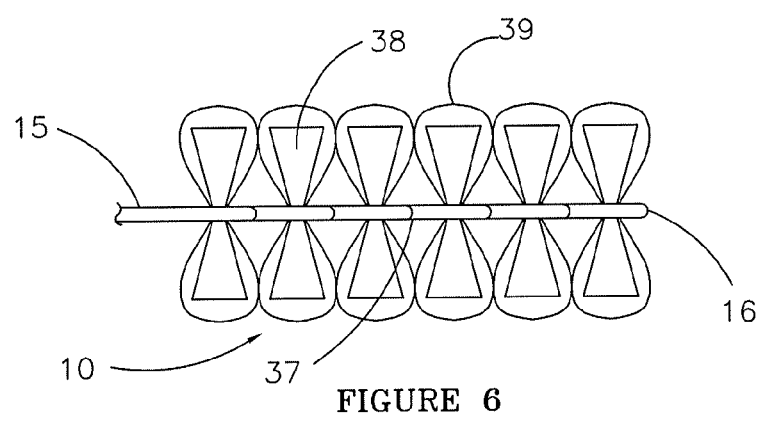
FIG. 6 is a graphical representation of a top view of the laser energy emission and fat liquefaction patterns of another method of use of the devices of FIGS. 1-3.

FIG. 6 illustrates laser energy emission area 38 and thermal diffusion area 39 of device 10 produced by positioning distal end 16 of liposuction cannula 15 in a series of steps at selected positions 37 and emitting laser energy at a selected level of laser energy and for a selected period of time at each position, depending on the thickness of the fatty layer and the rate of movement of the side firing device, as described above, with emission port 19 first positioned at about 3 o'clock and thereafter at about 9 o'clock, while repetitively rotating optical fiber 12, handpiece 14, cannula 15 and laser emission port 19 through an arc of about 120° from about 1 to 5 o'clock and thereafter from about 7 to 11 o'clock at the rate of rotation described earlier. Either of these orientations of side firing device 10 at 3 or 9 o'clock can precede the other.

Since cannula 15 is not being advanced or withdrawn and is maintained at each position 37 for the period of time described above, there is sufficient time at each position 37 to enable deeper penetration of laser energy and deeper diffusion of thermal energy into the fat layer to occur. As a result, laser energy area 38 and thermal diffusion area 39 are significantly larger than laser energy emission area 35 and thermal diffusion area 36 of FIG. 5.

However, even though the laser energy diverges as it exits port 19, there are regions close to the laser energy's exit point from port 19 in which fat cells may be inadequately lysed and the released fat inadequately softened or liquefied. This problem is solved, as described in the discussion of FIG. 7 below.

Figure 7:
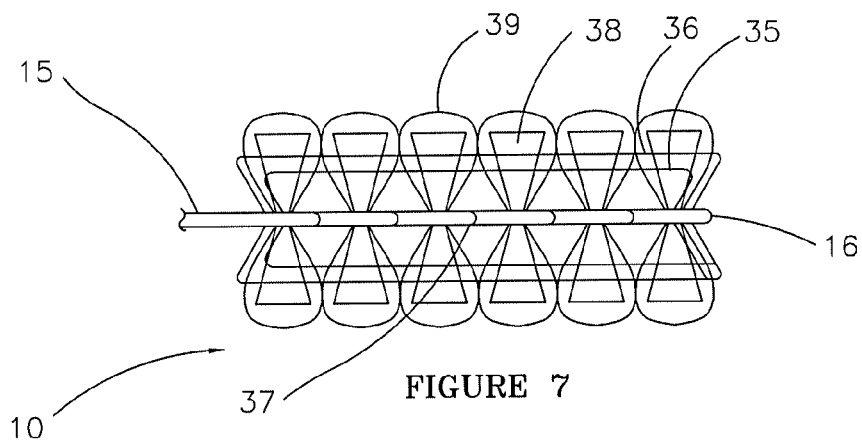
FIG. 7 is a graphical representation of a top view of the fat liquefaction pattern resulting from the combined methods of use of the devices of FIGS. 5 and 6.

FIG. 7 illustrates the effect of combining the methods of use of device 10 of FIGS. 1-3, as shown in FIGS. 5 and 6. As can be seen, advancing and/or withdrawing side firing device 10, while lasing and repetitively rotating side firing device 10, as described above, creates laser energy emission area 35 and thermal diffusion area 36 as shown in FIG. 5. Then, emitting laser energy in a series of steps at selected positions 37, as described in FIG. 6, creates larger laser emission area 38 and thermal diffusion area 39. The benefit of combining the laser emission patterns of FIGS. 5 and 6 results in more uniform lysing of fat cells softening and liquefying the released fat and evacuating a larger volume of fat from a larger area.

Alternatively, to accomplish the effect of sequentially performing the methods of FIGS. 5 and 6 described above, optical fiber 12, handpiece 14, cannula 15 and laser energy emission port 19 may be slowly advanced and withdrawn through the space between one position 37 and the next position 37, first at about 3 o'clock and then at about 9 o'clock, while repetitively rotating emission port 19 through an arc of about 120°, first from up to about 1 to 5 o'clock and, thereafter, from up to about 7 to 11 o'clock, as described above. Laser energy emission area, thermal diffusion area 36, laser energy emission area 38 and thermal diffusion area 39 of this procedure will be substantially the same as seen in FIG. 7.

Figure 8:
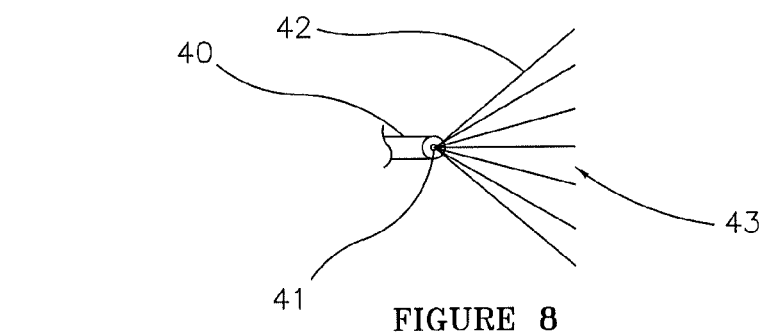
FIG. 8 is a graphical illustration of the directions in which conventional, prior art liposuction devices are used through one insertion point.

FIG. 8 illustrates, the use of a conventional, prior art laser liposuction device 40 employing a prior art liposuction cannula 41, in which conventional, straight ahead-firing optical fiber 42 is disposed. Conventional liposuction cannula 41 is inserted through one puncture site (not separately shown) and is advanced and withdrawn while emitting laser energy at a first insertion angle 43. Liposuction cannula 40 is then withdrawn, almost to the puncture site, and is then advanced and withdrawn while emitting laser energy at a second insertion angle 43. As this process is repeated, it results in lasing pattern 44, like the ribs of a fan.

While this limits the number of skin entry points, insertion angles 43 would not be feasible for the use of the present invention, which contemplates emitting laser energy laterally from the axis of optical fiber 12 as, near the junctions of insertion angles 43, overlapping lateral emissions of laser energy of device 10 of FIGS. 1-3 would cause overheating and by thermal diffusion or propagation, result in damage to or discoloration of the dermis above the junction of insertion angles 43.

Figure 9:
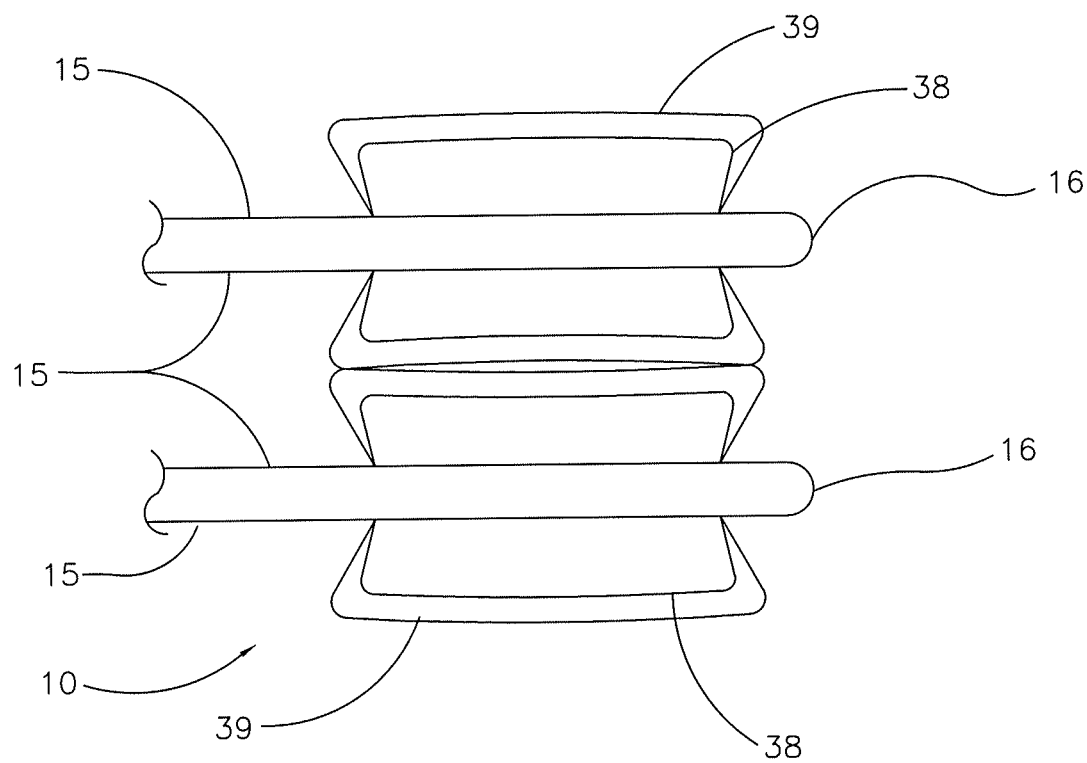
FIG. 9 is a graphical representation of a top view of the method of use of the device of the present invention through two insertion points.

FIG. 9, seen from above, shows the resulting larger laser energy emission areas 38 and larger thermal diffusion areas 39 which result from the combination of the smaller laser emission area 35 and smaller thermal diffusion area 36 of FIG. 5 with the larger area laser emission 38 and thermal diffusion area 39 of FIG. 6, respectively, due to the additional thermal diffusion this combination of procedures produces.

As shown, liposuction cannula 15 has been inserted through two, separate insertion points in a parallel fashion, while emitting laser energy according to the methods described in FIGS. 5 and 6, as seen in FIG. 7. Inserting device 10 through two or more separate puncture sites can produce nearly touching or overlapping areas of fat liquefaction, melting and extraction for a more uniform and cosmetically pleasing effect over large body areas, such as the abdomen, the posterior or the thighs. While only two insertion points are shown in FIG. 9, any number of insertion points may be used, depending on the size of the area of the body to be treated.

Other positionings of the side firing device 10 fixedly disposed within liposuction cannula 15, concomitantly used with suction and infusion of fluid through liposuction cannula 15, promptly followed by the use of liposuction cannula 15, the use of side firing device 10 by itself, without being followed by a liposuction procedure, at the laser energy levels, laser energy emission time periods and rate of movement and rotation rate of side firing device 10, as described in FIGS. 1-3 and 5-7, fixedly disposed within liposuction cannula 15, may also be employed to more safely and uniformly remove a greater volume of fat than can be achieved using a conventional, straight-ahead firing optical fiber used by itself, disposed within or followed by the use of a liposuction cannula, without departing from the principles of the invention described above.

Figure 10:
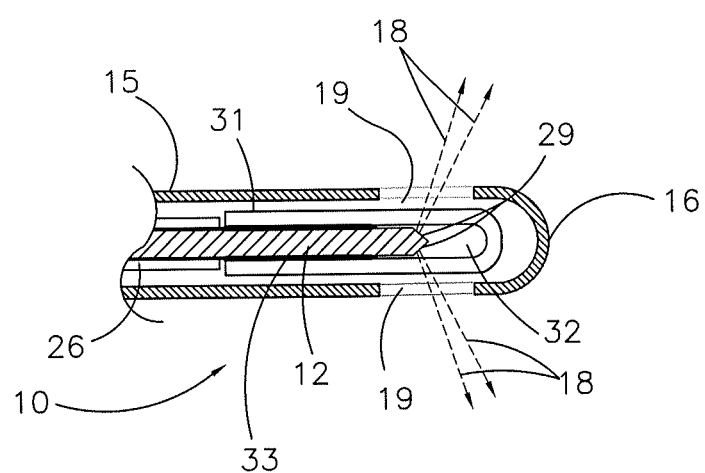
FIG. 10 is a cross-sectional, side view of an alternative embodiment of the devices of FIGS. 2 and 3.

FIG. 10 illustrates a preferred embodiment of the present invention, in which distal end 16 of cannula 15 is blunt ended or rounded, and two inclined, opposed but converging beveled surfaces 29 of optical fiber 12 form a chisel-like shaped distal end of optical fiber 12, which is sealingly encased in a distally closed-ended capillary tube 31, as described in FIG. 2 above.

Each of surfaces 29 is beveled at an angle of about 35° to 45°, preferably 40° to 41°, from the axis of optical fiber 12. Laser energy is simultaneously emitted from chisel-like shaped beveled surfaces 29 of optical fiber 12, relative to button 17 positioned at 12 o'clock, simultaneously at about 3 o'clock and about 9 o'clock, through ports 19, as indicated by arrows 18. Beveling each of surfaces 29 at an angle of about 40° to 41°, respectively, causes the laser energy to be most efficiently reflected by Snell's Law at an angle of about 80° to 82° from the axis of optical fiber 12, as shown by arrows 18, while repetitively rotating handpiece 14 and emission ports 19 through an arc of about 120°, as described above.

Likewise, the distal end of optical fiber 12 can be beveled with two opposed surfaces 29 forming a chisel-like distal end of optical fiber 12 (not separately shown), without encasing the distal end portion of optical fiber 12 in a closed-ended capitally tube (not separately shown), as described with respect to FIG. 3, for use with laser energy at wavelengths of 195 to 400 nm, 400 to 1400 nm and 1500 to 1800 nm, to simultaneously emit laser energy at about 3 and 9 o'clock, to accomplish the same effect.

Likewise, the inclined surface 28 of the cavity in metal tip 27, as described in FIG. 1, may also be formed with two chisel-like shaped surfaces 29 (not separately shown), each beveled at an angle of about 35° to 50°, preferably at about 45°, to simultaneously reflect laser energy at about 3 o'clock and 9 o'clock to accomplish the same effect.

The benefit of this embodiment is liposuction cannula 15 containing side firing device 10 can be positioned and simultaneously emit laser energy at 3 o'clock and 9 o'clock, without having to first position liposuction cannula 15 and side firing device 10 to emit laser energy at about 3 o'clock and then reposition cannula 15 and device 10 to emit laser energy at about 9 o'clock. Since laser energy is emitted from two emission ports 19 of substantially equal cross-sectional areas in liposuction cannula 15, the amount of laser energy must be doubled, the time of lasing at each selected position 37 must be doubled or the rate of advancement and withdrawal of liposuction cannula 15 must be halved, or vice-versa, to achieve the same fat liquefaction effect. Also, since each of ports 19 will be of about the same size, about twice the negative vacuum pressure will be required to evacuate by suction the larger volume of fat being liquefied.

Device 10 of FIG. 10 can also be used by itself or its use can be promptly followed by the use of a liposuction cannula, or not, whichever the physician desires for a particular patient.

Figure 11:
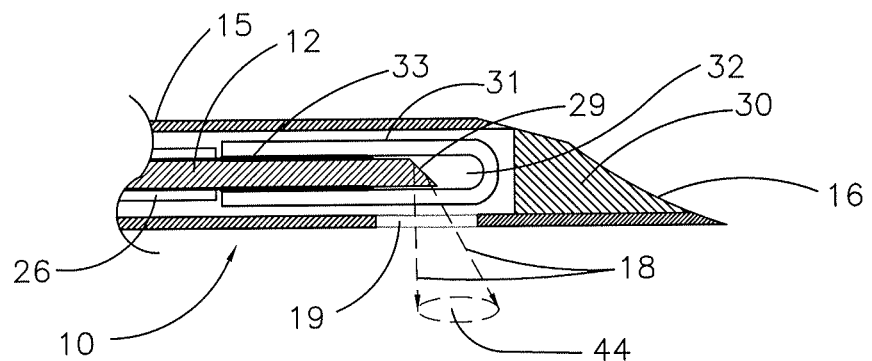
FIG. 11 is a cross-sectional, side view of the device of FIG. 2, showing its laser emission spot size.

FIG. 11 illustrates optical fiber 12 of device 10 of FIG. 2, whose beveled, distal end surface 29 has been beveled at an angle of about 35° to 45°, preferably about 40° to 41°, from the axis of optical fiber 12, and is sealingly encased in distally closed-ended capillary tube 31 with a wall thickness of about 500 microns, and laser energy is emitted at an angle of 80° to 82° from each of beveled, distal end surfaces 29 of optical fiber 12 through port 19, as shown by arrows 18, to form laser spot area 44 on or within a tissue (not separately shown).

Figure 12:
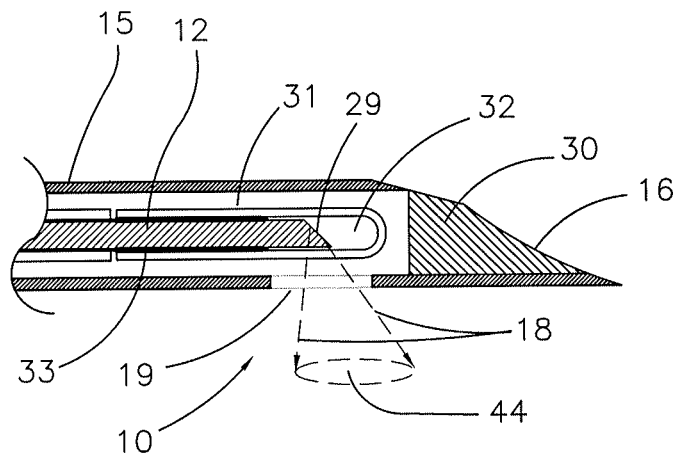
FIG. 12 is a sectional side view of a preferred embodiment of the device of FIG. 2, showing its laser emission spot size.

As shown in FIG. 12, optical fiber 12 is sealingly encased within a distally closed-ended capillary tube 31 with a substantially thinner wall thickness, preferably about 350 microns, which reduces the amount of cylindrical lensing that occurs and converges the divergent output of laser energy from beveled, distal end surface 29 of optical fiber 12 at a closer point, providing an effectively wider angle of divergence at a given distance from laser energy emission port 19, as illustrated by arrows 18 and larger laser spot area 44 on or within a tissue (not separately shown).

Figure 13:
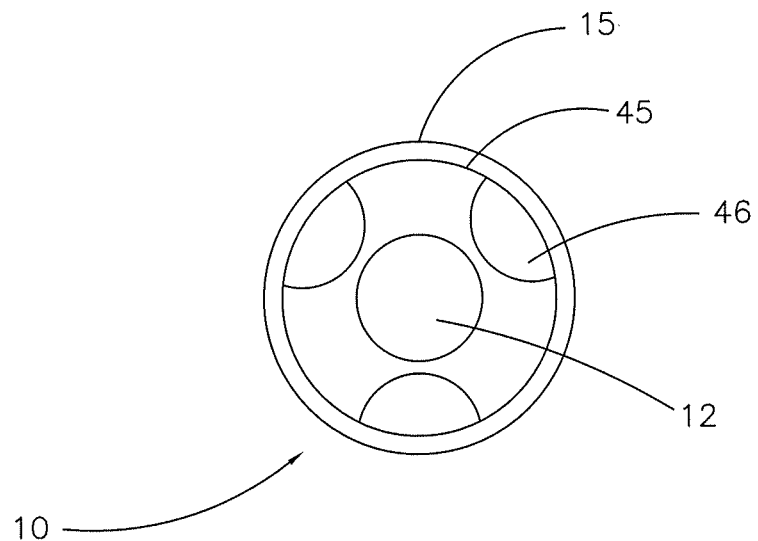
FIG. 13 is an end view of a preferred embodiment of the devices of FIGS. 1-3 and 10-12.

The benefit of device 10 of FIG. 12 is that optical fiber 12, handpiece 14, cannula 15 and emission port 19 of device 10 of FIG. 2 may be rotated through an arc of only about 90° and create a wider area of fat cell lysing and a greater volume of fat softening, liquefaction and extraction than possible with side firing device 10 of FIGS. 1-3 or that of FIG. 11, FIG. 13 illustrates another preferred embodiment of the device of the present invention. To support and position optical fiber 12 in the center of liposuction cannula 15, cannula 15 is extruded with at least one longitudinally extending ridge or rib 46, preferably at least three ribs 46, each extending inwardly from inner surface 47 of liposuction cannula 15 a distance sufficient to sealingly contact the exterior surface of optical fiber 12. While FIG. 13 illustrates three ribs 46, any other number of ribs 46 may be employed.

Ribs 46 should preferably terminate just proximal to laser energy emission port 19 of FIGS. 1-3 or ports 19 of FIG. 10. Alternatively, ribs 46 may be positioned so ribs 46 are not in the path of laser energy being emitted from laser energy emission port or ports 19. If four ribs 46 are utilized in liposuction cannula 15 of FIG. 10 with two ports 19, for example, four ribs 46 may be positioned, at 30°, 150°, 210° and 330° from 12 o'clock, where 12 o'clock is the skin (not separately shown), so as not to obstruct the emission of laser energy from ports 19. Ribs 46 may also be positioned at other points on inner surface 47 of liposuction cannula 15 to achieve the same purpose.

If, for example, three ribs 46 are extruded in cannula 15, as described above, vacuum may be applied to the space between one pair of ribs 46, the inner surface of cannula 15 and the exterior surface of optical fiber 12 to extract liquefied fat, and a liquid, such as saline, saline containing an anesthetic or saline containing an anesthetic and a vasoconstrictor and/or an antibiotic, as known in the art, may be infused by means known in the art through the space between the other two pairs of ribs 46, to anesthetize, vasoconstrict and/or reduce the risk of an infection, as well as to expand the space between layers of fat.

If, for example, five ribs 46 are used, vacuum may be applied to the spaces between three pairs of ribs 46, and the liquid described above may be infused through to the space between the other pair of ribs 46. Of course, any number of ribs 46 may be used to center optical fiber 12 within cannula 15, and vacuum or infusion of said liquid can be applied to any desired number of pairs of ribs.

To assure that such liquid exits the space between at least one pair of ribs 46 and is not immediately drawn into port 19 of cannula 15 by suction, the pressure applied to infusion of the liquid should exceed by at least a small margin the negative pressure created by the vacuum applied to the space between at least one other pair of ribs 46.

Figure 14:
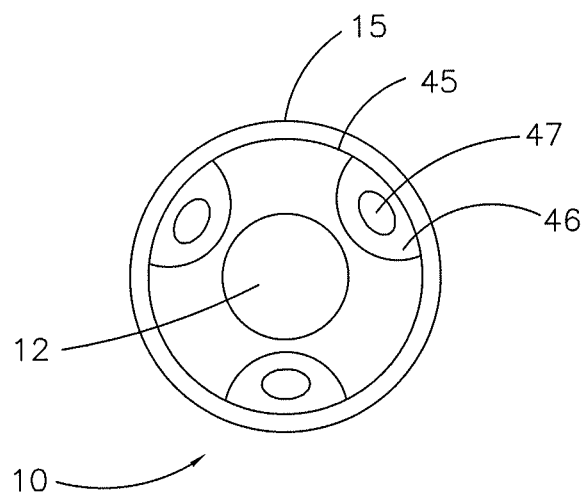
FIG. 14 is an end view of a more preferred embodiment of the devices of FIGS. 1-3 and 10-12.

FIG. 14 illustrates a more preferred embodiment of the device of the present invention. In this embodiment, at least one rib 46 is extruded with a fluid channel 48 extending longitudinally through its length. Fluid channel 47 may be round, elliptical or of any other shape. Preferably, all ribs 46 have a fluid channel 47, and a vacuum can be applied to any or all of the spaces between ribs 46.

Again, saline containing an anesthetic, or saline containing both an anesthetic and a vasoconstrictor, with or without an antibiotic, should be infused through fluid channel or channels 48 at a pressure at least slightly greater than the negative pressure of the suction applied to port or ports 19 of cannula 15.

The infusion of saline, saline containing a vasoconstrictor or saline containing an anesthetic and a vasoconstrictor, with or without an antibiotic, in addition to reducing any pain or sensation of intrusion of cannula 15 and reducing the risk of an infection, can absorb and carry-away any excessive amount of heat produced in the area close to emission port or ports 19 in cannula 15, increasing the safety and comfort of the laser fat removal procedure.

Figure 15:
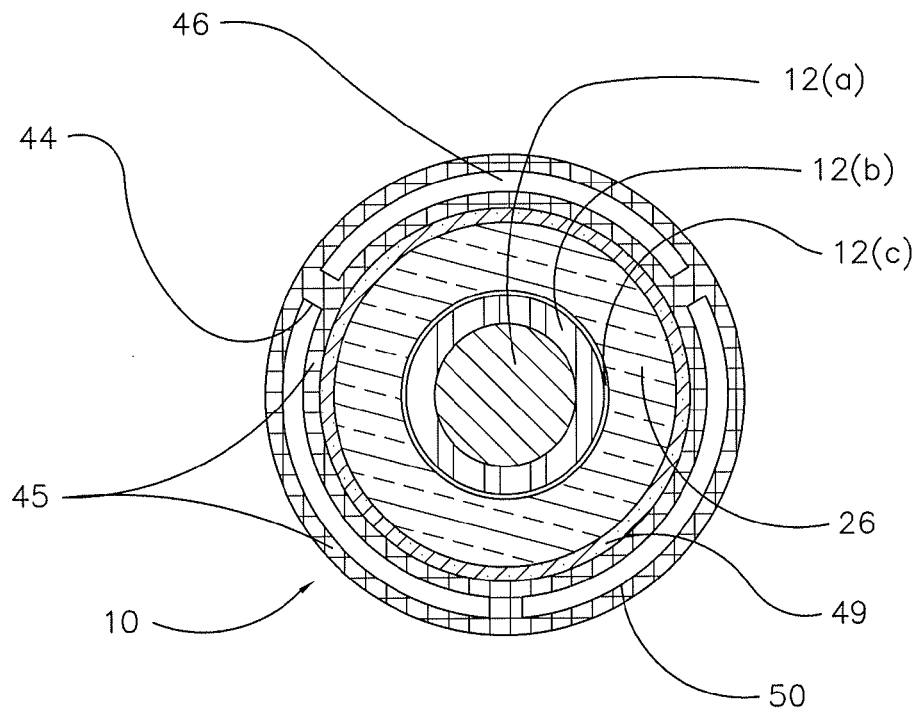
FIG. 15 is an exterior, side view of an alternate embodiment of the present invention.

FIG. 15 is a cross sectional view of a very small diameter device 10 for use in lysing of fat cells and melting the released fat, shown at a point proximal to capillary tube 31. Instead of optical fiber 12 having a customary 550 to 600 micron core diameter, in this embodiment of the present invention, fused silica optical fiber 12 has a core 12(a) diameter of 365 microns and an outer, fluorine doped, fused silica cladding 12(b) with a wall thickness of 17 microns, and an undoped, fused silica cladding 12(c) with a wall thickness of 18 microns, for a combined optical fiber and cladding O.D. of 400 microns. The body of optical fiber 12, proximal to capillary tube 31, is covered by an optional plastic cladding 12(d) and a protective buffer coating 26 to protect the fragile core 12(a) of optical fiber 12 from excessive bending and mechanical damage, for an overall optical fiber 12 O.D. of 550 microns. Optical fiber 12 extends from optical coupler 13 of laser energy source 11 into handpiece 14 and through a lengthwise passageway 34 in handpiece 14 (not separately shown) and through rigid plastic or metal sleeve 49.

Optionally, as shown in FIG. 15, optical fiber 12 may extend through double walled, flexible cannula 50, which can be extruded with at least two vertical ribs 44, preferably at least three ribs 44, extending between the two walls 45 of cannula 50 to hold them apart in a fixed position relative to one another, creating channels 46. Cannula 50 extends over sleeve 49, up to the proximal end of capillary tube 31(not separately shown). The proximal end of cannula 50 may be fixedly attached within the distal end of lengthwise passageway 34 in handpiece 14 and be in fluid communication with channel 34 of handpiece 14, luer fitting 20 in the wall of handpiece 14, and suction line 22 to collection bottle 23.

The distal end portion of optical fiber 12 has been bared of buffer coating 26 and any optional polymer cladding 12(c), prior to attaching fused silica capillary tube 31 to bared optical fiber 12.

The distal end of bared optical fiber 12 has been beveled at an angle of 35° to 45°, preferably about 40° to 41°.

Capillary tube 31 is close fitted over bared optical fiber 12, with a gap not exceeding 25 microns, creating an air environment opposite the beveled, distal end surface 29 of optical fiber 12, required for total internal reflection of laser energy. The proximal end of capillary tube 31 is fixedly attached to bared optical fiber 12 by adhesive 33, which is substantially transparent to laser energy from CTH:YAG, diode, KTP Nd:YAG and other lasers commonly used in medical procedures, does not appreciably absorb such wavelengths of laser energy and does not melt from back-transmitted laser energy, avoiding capillary tube 31 from being detached from bared optical fiber 12.

To additionally prevent capillary tube 31 from being detached from optical fiber 12, the junction between the proximal end portion of capillary tube 31 and buffer coating 26 of optical fiber 12 is covered by shrink wrap 51 made of one of a variety of medical grade, heat shrinkable plastics that are commercially available, which may also be fixedly attached to capillary tube 31 and buffer coat 26 of optical fiber 12 by adhesive 33, which prevents absorption of laser energy overheating and dislodgment of capillary tube 31 from optical fiber 12.

As seen in FIG. 15, double-walled cannula 50 is extruded with at least two ribs 44 extending lengthwise from the inner wall to the outer wall, of the two concentrically walled cannula 50, to create at least two spaces there between, one for vacuum and one for infusion of an irrigation fluid. The space between one set of ribs 44 can have its own luer fitting (not separately shown) for infusion of an irrigation fluid. The space between the other ribs 44 can be in fluid communication with lengthwise passageway 34 in handpiece 14 and its luer fitting 20, as described in FIG. 3, to a source of a vacuum (not separately shown).

Figure 16:
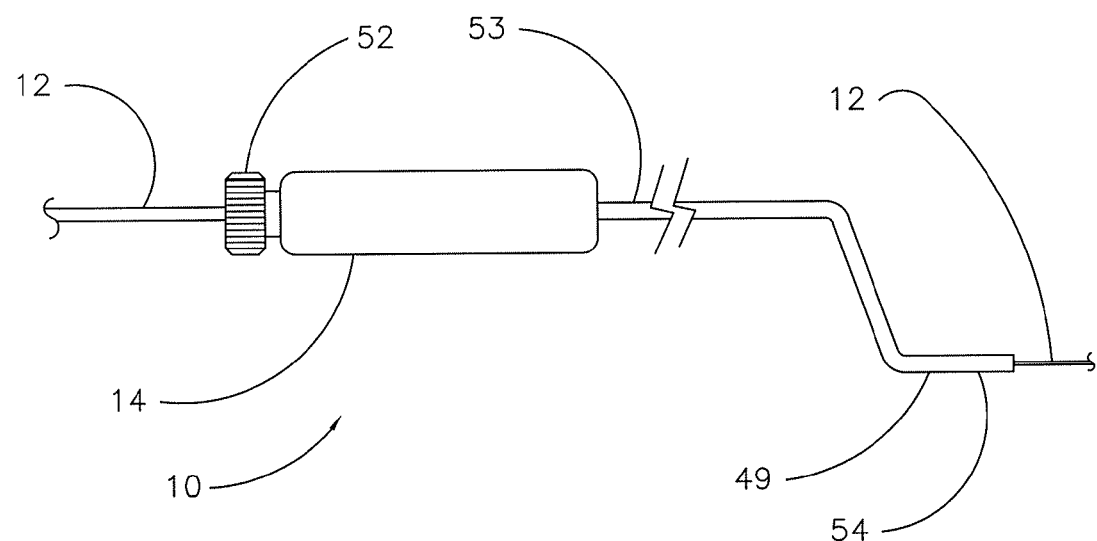
FIG. 16 shows another device suitable for practicing the methods of the present invention.

As shown in FIG. 16, metal or rigid plastic sleeve 49, preferably made of medical grade stainless steel, extends from the distal end of handpiece 14. Optical fiber 12 passes through and can be removably fixed in place within compression fixture 52. Metal or plastic sleeve 49 has two bends of 70° to 90°, respectively, which places the lower surface of handpiece 14 and the lower surface of the upper portion 53 of sleeve 49 at least 2 cm above the lower surface of the lower portion 54 of sleeve 49, providing space for the operator's fingers.

Optical fiber 12 has a sufficiently small in O.D. to pass through both 70° to 90° bends in sleeve 49, without any significant loss of laser energy or breakage. Without the space for the operator's fingers between the upper and lower portions of sleeve 49, optical fiber 12 exiting sleeve 49, with the distal end of optical fiber 12 beveled at an angle of 40° to 41° and disposed within attached capillary tube 31, they would enter tissue at a downward angle, passing through the adipose layer and into deeper structures, which would not be desirable.

Figure 18:
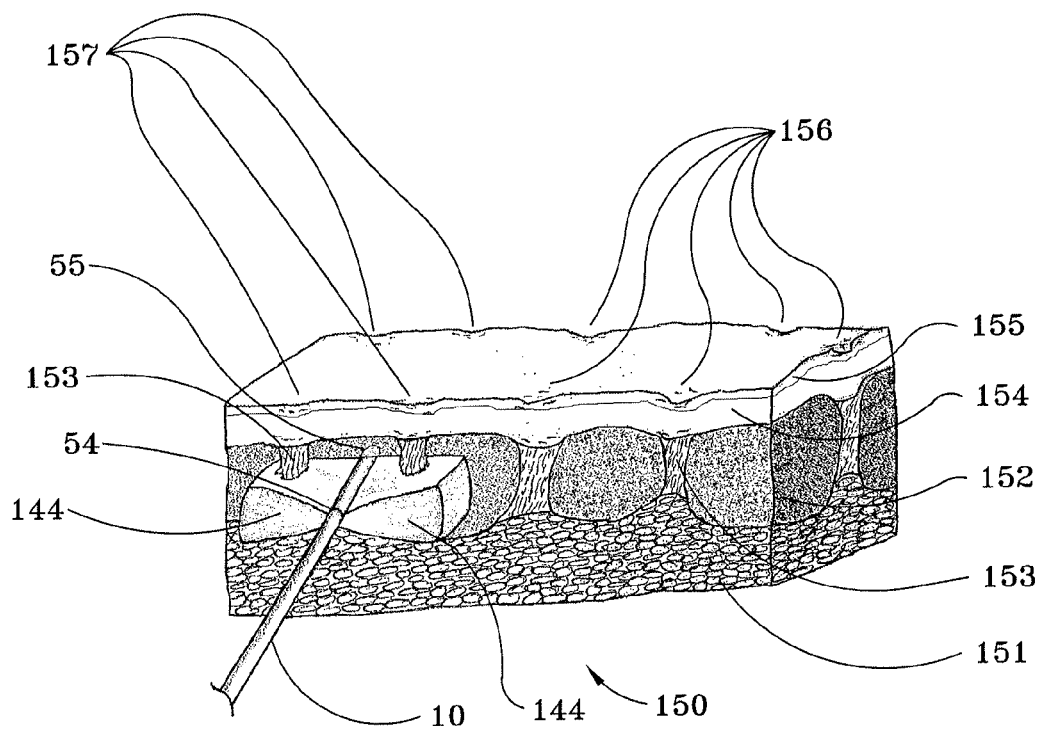
FIG. 18 is a partial, cut-through, side view of the epidermis, dermis and subdermal tissues.

FIG. 18 illustrates a lipolysis procedure using side firing device 10. Thermal Energy is applied to sub-dermal tissues 150 consisting of thickened, hypodermal fat lobule layer 151, adipocyte (fat cell) layer 152 and fibrous septae 153, which extend from fat lobule layer 151, through adipocyte layer 152 to dermis 154 beneath epidermis layer 155. The emission of laser energy lyses the cell walls of fat lobule layer 151 and adipocyte layer 152 and melts released fat to reduce unsightly sub-dermal fat deposits.

Fibrous septae 153, which separate sections of fat lobule layers 151 and extend from fat lobule layers 151 to dermis 154, and, due to an unknown cause, sometimes shrink, retracting dermis 154 and epidermis 155, resulting in deep dimples 156, called cellulite. Emission of laser energy in the bowtie-like vaporization pattern 144, as described above, vaporizes and cuts fiborous septae 153 to release their tension on dermis 154 and epidermis 155, and reduces or eliminates the deep skin dimples known as cellulite.

A rigid side firing device 10 of FIG. 1-4 or 6-8, can be manipulated, while laser energy is emitted, with concurrent continuous sterile irrigation fluid flow, from first position 54 to second position 55, while simultaneously cycling device 10 through an arc of about 90°, first from about 2 to 4 o'clock and then from about 8 to 10 o'clock (or through an arc of 120°, first from 1 to 5 o'clock and then from 7 to 11 o'clock), creating bowtie-like laser energy irradiation pattern 144.

Bowtie-like irradiation pattern 144 can (a) alter by lysing the membranes of fat lobules 151 and adipocytes 152, (b) alter by melting the released fat (not separately shown) and (c) alter by vaporizing or cutting fibrous septae 153, which releases the tension on dermis 154 and epidermis 155, reducing unsightly subdermal fat acculations and causing the relaxation or disappearance of deep dimples 156, resulting in very shallow dimples 157, or none at all.

The released fat may enter the bloodstream and be carried to the liver, where it may be metabolized. Alternatively, to reduce the risk of excess melted fat remaining in sub-dermal tissues, the use of rigid, side firing devices 10 of FIG. 1-4 or 6-8, as described above, can be promptly followed by a conventional liposuction procedure to remove the melted fat.

For more safe and effective removal of the melted fat, any of rigid, side firing devices 10 of FIG. 1-4 or 6-8 may be disposed within a conventional liposuction cannula, with a port or ports opposite each point of laser energy emission (not separately shown). Laser energy is emitted during the liposuction procedure, lysing the cell membranes of fat lobules 151 and/or adipocytes 152 and melting the released fat, which is simultaneously removed by suction to a collection bottle.

The liposuction cannula may be manipulated in separate steps or simultaneously, to Sweep the laser energy through a swath of fat lobules 151, adipocytes 152 and fibrous septae 153, in the bowtie-like irradiation pattern 144 described above.

At the same time the fibrous septae 153 are cut, releasing their tension on dermis 154 and epidermis 155, reducing or eliminating cellulite.

Alternatively, electro-shock wave ("ESW") energy may be focused on fat lobule layer 151, adipocyte layer 152, and fibrous septae 153 to fragment and destroy them, accomplishing the same effect as described above.

Figure 17:
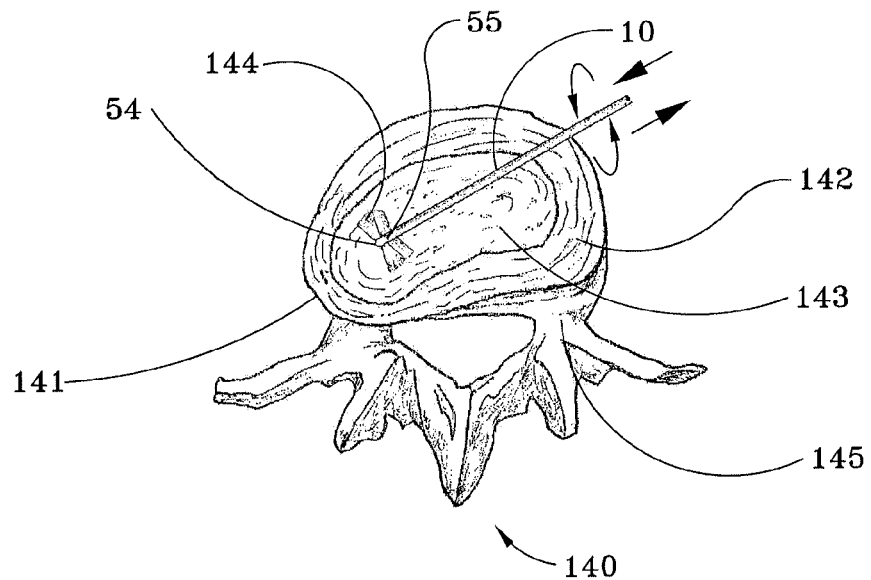
FIG. 17 is a cut-through, top view of a spinal disc, in which the nucleus pulposus is being vaporized, using the above-described bowtie-like laser energy vaporization pattern.

The same devices 10 of FIG. 1-3 or 10-12 can be used in the manner described in FIGS. 4-6 for a similar purpose, to vaporize excess nucleus pulposus tissue 143 (FIG. 17) which is causing annulus 142 of spinal disc 141 to bulge outwardly, pressing upon nerves running alongside annulus 142, causing unrelenting pain. When sufficient nucleus pulposus tissue is removed by applying bowtie-shaped laser energy emission pattern 144, as described above, the pressure on annulus 142 and the surrounding nerves is relieved, and the pain ceases.

If the herniation of annulus 142 is very large, device 10 of FIG. 1-3 or 10-12 can be advanced or withdrawn, for example, about 1 cm, and bowtie-shaped laser energy emission pattern 144 can be repeated.

While this invention is susceptible of embodiment in many different forms, there are shown in the drawings and will be described in detail herein specific embodiments thereof, with the understanding that the present disclosure is to be considered as an exemplification of the principles of the invention and is not to be limited to the specific embodiment illustrated.

Numerous variations and modifications of the embodiments described above can be effected without departing from the spirit and scope of the novel features of the invention. It is to be understood that no limitation with respect to the specific apparatus illustrated herein is intended or should be inferred. It is, of course, intended to cover by the appended claims, all such modifications as fall within the scope of the claims.

The invention claimed is:

1. A method for vaporizing excess nucleus pulposus tissue comprised of the steps:

introducing into the nucleus pulposus tissue a side firing device and irradiating with said side firing device said tissue with laser energy of a desired wavelength at a desired energy level for a desired period of time, depending on the density and volume of tissue to be vaporized while the side firing device is cycled repetitively through an arc of about 120 degrees and advanced into the tissue at a rate of about 1 to 5 centimeters per second.

2. The method of claim 1 wherein the irradiation is effected while the side firing device is cycled repetitively through an arc of about 120 degrees and advanced into the tissue at a rate of about 2 to 3 centimeters per second.

3. The method of claim 1 wherein the irradiation is effected while the side firing device is cycled repetitively through an arc of up to about 120 degrees at a rate of about one cycle each 0.5 to 2 seconds.

4. The method of claim 1 wherein the irradiation is effected while the side firing device is cycled repetitively through an arc of up to about 120 degrees at a rate of about one cycle each second.

5. The method of claim 1 wherein the irradiation is effected at a power level in the range of about 2 to 30 watts.

6. The method of claim 1 wherein the irradiation is effected at a power level in the range of about 5 to about 20 watts.

7. The method of claim 1 wherein the irradiation is effected at a power level in the range of about 0.05 to 10 watts and without irrigation liquid infusion.

8. The method of claim 1 wherein the irradiation is effected at a power level in the range of about 0.1 to about 5 watts and without irrigation liquid infusion.

* * * * *